US012606630B2

(12) United States Patent
Braunschweig

(10) Patent No.: US 12,606,630 B2
(45) Date of Patent: Apr. 21, 2026

(54) CD25 CHIMERIC ANTIGEN RECEPTORS AND USES THEREOF

(71) Applicant: Montefiore Medical Center, Bronx, NY (US)

(72) Inventor: Ira Braunschweig, Woodmere, NY (US)

(73) Assignee: MONTEFIORE MEDICAL CENTER, Bronx, NY (US)

( * ) Notice: Subject to any disclaimer, the term of this patent is extended or adjusted under 35 U.S.C. 154(b) by 937 days.

(21) Appl. No.: 17/753,364

(22) PCT Filed: Aug. 28, 2020

(86) PCT No.: PCT/US2020/048574
§ 371 (c)(1),
(2) Date: Feb. 28, 2022

(87) PCT Pub. No.: WO2021/041936
PCT Pub. Date: Mar. 4, 2021

(65) Prior Publication Data
US 2022/0324987 A1 Oct. 13, 2022

Related U.S. Application Data

(60) Provisional application No. 62/893,039, filed on Aug. 28, 2019.

(51) Int. Cl.
*C07K 16/28* (2006.01)
*A61K 38/00* (2006.01)
(Continued)

(52) U.S. Cl.
CPC .......... *C07K 16/2866* (2013.01); *A61K 40/11* (2025.01); *A61K 40/31* (2025.01);
(Continued)

(58) Field of Classification Search
CPC ................ C07K 16/2866; C07K 14/55; C07K 14/7051; C07K 14/70517;
(Continued)

(56) References Cited

U.S. PATENT DOCUMENTS

2018/0162939 A1     6/2018  Ma et al.
2020/0283534 A1*    9/2020  Ma ......................... A61K 40/42

FOREIGN PATENT DOCUMENTS

WO    WO-2013051718 A1 *   4/2013    .............. A61P 35/00
WO    WO-2016138491 A1 *   9/2016    .............. A61K 35/17
WO    WO-2019192526 A1 *  10/2019    .............. A61K 35/17

OTHER PUBLICATIONS

International Search Report and Written Opinion for PCT/US2020/48574, dated Dec. 2, 2020, 9 pages.
(Continued)

*Primary Examiner* — Tracy Vivlemore
*Assistant Examiner* — Thomas R. Amick
(74) *Attorney, Agent, or Firm* — Perkins Coie LLP

(57) ABSTRACT
Provided herein are CD25 chimeric antigen receptors and compositions and methods for using the same. Methods for using CD25 chimeric antigen receptors provided herein include, for example, methods of treatment, methods of enhancing the immune system in a subject, and methods of killing a target cell or a population of target cells.

19 Claims, 19 Drawing Sheets
Specification includes a Sequence Listing.

(51) Int. Cl.

| | |
|---|---|
| *A61K 39/00* | (2006.01) |
| *A61K 40/11* | (2025.01) |
| *A61K 40/31* | (2025.01) |
| *A61K 40/42* | (2025.01) |
| *A61P 35/00* | (2006.01) |
| *C07K 14/55* | (2006.01) |
| *C07K 14/705* | (2006.01) |
| *C07K 14/725* | (2006.01) |
| *C12N 15/86* | (2006.01) |

(52) U.S. Cl.
CPC .......... *A61K 40/4224* (2025.01); *A61P 35/00* (2018.01); *C07K 14/55* (2013.01); *C07K 14/7051* (2013.01); *C07K 14/70517* (2013.01); *C07K 14/70521* (2013.01); *C07K 14/70578* (2013.01); *C12N 15/86* (2013.01); *A61K 38/00* (2013.01); *A61K 2039/54* (2013.01); *C07K 2317/53* (2013.01); *C07K 2319/02* (2013.01); *C07K 2319/03* (2013.01); *C07K 2319/33* (2013.01); *C12N 2740/10043* (2013.01); *C12N 2740/15043* (2013.01)

(58) Field of Classification Search
CPC ........ C07K 14/70521; C07K 14/70578; C07K 2317/53; C07K 2319/02; C07K 2319/03; C07K 2319/33; C07K 2317/622; A61K 40/11; A61K 40/31; A61K 40/4224; A61K 38/00; A61K 2039/54; A61P 35/00; C12N 15/86; C12N 2740/10043; C12N 2740/15043

See application file for complete search history.

(56) References Cited

OTHER PUBLICATIONS

Zheng et al., "IL-2 Receptor-Targeted Cytolytic IL-2/Fc Fusion Protein Treatment Blocks Diabetogenic Autoimmunity," Nonobese Diabetic Mice. J Immunol, Oct. 1, 1999, vol. 163, No. 7, p. 4041-4048.

UniProt submission Q0GK43 (QOGK43_HUMAN) *Homo sapiens* (Human) Interleukin-2, Oct. 3, 2006 [online]. [Retrieved on Nov. 8, 2020].

* cited by examiner

| Lot No. | N.A. | | Cloning Vector | pMSGV |
|---|---|---|---|---|
| Cloning Sites | CloneEZ | | Insert Size | 1260 bp |

| QC Results | | |
|---|---|---|
| Test Items | Specifications | Results |
| Insert Sequence | Insert sequence results consistent with target | Pass |
| Vector Sequence | Flanking sequence consistent with expected | N/A |
| ORF Across Junction | Correct and consistent with target | N/A |
| Restriction Digest | Expected fragment sizes observed | N/A |
| PCR Amplification | Correct without non - specific bands | Pass |
| DNA Quantity/Quality | Actual yield (by A 260) | 10 μg/tube |
| | Concentration (n/a if lyophilized) | 200 ng/μL |
| | Purity (A 260/A280 = 1.8 – 2.0) | Pass |
| | # of Tubes | 1 |
| | Matrix | TE (lyophilized) |
| Endotoxin Test | Verified, <0.1 EU/μg (Endo-Free Preps Only) | N/A |
| Appearance | Clear, no visible particles | Pass |
| Label | Correct and white | Pass |

Restriction Digestion Map

Lane 1:
Plasmid
Lane 2:
Plasmid digested with Nhe I
Lane M:
DNA Marker

```
                    380       390       400       410       420       430
                    AGAGCAAGAACTTCCACCTGAGGCCTAGGGACCTGATCAGCAACATCAACGTGATCGTGCTG

A02-Y92833-C473FED150-2-2V-SEQF.ab1 (1>838)  →  AGAGCAAGAACTTCCACCTGAGGGCCTAGGGACCTGATCAGCAACATCAACGTGATCGTGCTG
C473FED150-2.seq(1>1261)                      →  AGAGCAAGAACTTCCACCTGAGGGCCTAGGGACCTGATCAGCAACATCAACGTGATCGTGCTG 440       450       460       470       480       490
                    GAACTGAAAGGCAGCGAGGAGACAACCTTCATGTGCGAGTACGCCGACGAGCAGCTACCATCGT A02-Y92833-C473FED150-2-2V-SEQF.ab1 (1>838)  →  GAACTGAAAGGCAGCGAGGAGACAACCTTCATGTGCGAGTACGCCGACGAGCAGCTACCATCGT
C473FED150-2.seq(1>1261)                      →  GAACTGAAAGGCAGCGAGGAGACAACCTTCATGTGCGAGTACGCCGACGAGCAGCTACCATCGT
A03-Y92833-C473FED150-2-2-SEQ1.ab1 (1>843)   →  AcGAGACAGCTACCATCGT 500       510       520       530       540       550
                    GGAATTTCTGAACCGGTGGATCACGTTCTGCCAGAGGCATCATCAGCACCCTGACCACCACGA A02-Y92833-C473FED150-2-2V-SEQF.ab1 (1>838)  →  GGAATTTCTGAACCGGTGGATCACGTTCTGCCAGAGGCATCATCAGCACCCTGACCACCACGA
C473FED150-2.seq(1>1261)                      →  GGAATTTCTGAACCGGTGGATCACGTTCTGCCAGAGGCATCATCAGCACCCTGACCACCACGA
A03-Y92833-C473FED150-2-2-SEQ1.ab1 (1>843)   →  GGAATTTCTGAACCGGTGGATCACGTTCTGCCAGAGGCATCATCAGCACCCTGACCACCACGA 560       570       580       590       600       610       620
                    CGCCAGCGGCGCGACCGCGACCACCAACACCGGCGCGCCCACCATCGGCGTCGGCAGCGCCCTGTCCCTGCGC A02-Y92833-C473FED150-2-2V-SEQF.ab1 (1>838)  →  CGCCAGCGGCGCGACCGCGACCACCAACACCGGCGCGCCCACCATCGGCGTCGGCAGCGCCCTGTCCCTGCGC
C473FED150-2.seq(1>1261)                      →  CGCCAGCGGCGCGACCGCGACCACCAACACCGGCGCGCCCACCATCGGCGTCGGCAGCGCCCTGTCCCTGCGC
A03-Y92833-C473FED150-2-2-SEQ1.ab1 (1>843)   →  CGCcagCGGCGCGACCGCGACCACCAACACCGGCGCGCCCACCATCGGCGTCGGCAGCGCCCTGTCCCTGCGC 630       640       650       660       670       680
                    CCAGAAGCGGTGCCGGCCAGCGGGGGGGGGGCCGGCAGTGCCACACGAGAGGGGCTGGACTTCGGCCTG A02-Y92833-C473FED150-2-2V-SEQF.ab1 (1>838)  →  CCAGAAGCGGTGCCGGCCAGCGGGGGGGGGGCCGGCAGTGCCACACGAGAGGGGCTGGACTTCGGCCTG
C473FED150-2.seq(1>1261)                      →  CCAGAAGCGGTGCCGGCCAGCGGGGGGGGGGCCGGCAGTGCCACACGAGAGGGGCTGGACTTCGGCCTG
A03-Y92833-C473FED150-2-2-SEQ1.ab1 (1>843)   →  CCAGAAGCGGTGCCGGCCAGCGGGGGGGGGGCCGGCAGTGCCACACGAGAGGGGCTGGACTTCGGCCTG
```

*FIG. 3 (Cont.)*

```
                690       700       710       720       730       740
                |    |    |    |    |    |    |    |    |    |    |    |
      TGATATCTACACATTTGGGCCCCTCTGGCTGGTACTTGCCGGGTCCTGCTGCTTTCACTCGTGA

A02-Y92833-C473FED150-2-2V-SEQF.ab1 (1>838)  →  TGATATCTACACATTTGGGCCCCTCTGGCTGGTACTTGCCGGGTCCTGCTGCTTTCACTCGTGA
C473FED150-2.seq(1>1261)                      →  TGATATCTACACATTTGGGCCCCTCTGGCTGGTACTTGCCGGGTCCTGCTGCTTTCACTCGTGA
A03-Y92833-C473FED150-2-2-SEQ1.ab1 (1>843)   →  TGATATCTACACATTTGGGCCCCTCTGGCTGGTACTTGCCGGGTCCTGCTGCTTTCACTCGTGA 750       760       770       780       790       800
                |    |    |    |    |    |    |    |    |    |    |    |
      TCACTCTTTACTGTAGGAGCAAGCGGAGCAGACTGCTGCACAGCGACTACATGAACATGACC A02-Y92833-C473FED150-2-2V-SEQF.ab1 (1>838)  →  TCACTCTTTACTGTAGGAGCAAGCGGAGCAGACTGCTGCACAGCGACTACATGAACATGACC
C473FED150-2.seq(1>1261)                      →  TCACTCTTTACTGTAGGAGCAAGCGGAGCAGACTGCTGCACAGCGACTACATGAACATGACC
A03-Y92833-C473FED150-2-2-SEQ1.ab1 (1>843)   →  TCACTCTTTACTGTAGGAGCAAGCGGAGCAGACTGCTGCACAGCGACTACATGAACATGACC 810       820       830       840       850       860
                |    |    |    |    |    |    |    |    |    |    |    |
      CCCGGGAGGCCTGGCCCCACCCGGAAGGACTACCAGCCCTACGCCCCTCGC A02-Y92833-C473FED150-2-2V-SEQF.ab1 (1>838)  →  CCCGGGAGGCCTGGCCCCACCCGGAAGGACTA
C473FED150-2.seq(1>1261)                      →  CCCGGGAGGCCTGGCCCCACCCGGAAGGACTACCAGCCCTACGCCCCTCGC
A03-Y92833-C473FED150-2-2-SEQ1.ab1 (1>843)   →  CCCGGGAGGCCTGGCCCCACCCGGAAGGACTACCAGCCCTACGCCCCTCGC 870       880       890       900       910       920       930
                |    |    |    |    |    |    |    |    |    |    |    |    |    |
      CGGCCTACCGGGAGCAAACGGGGCAGAAAGAAACTCCTGTATATATTCAAACAACCATTTATGA C473FED150-2.seq(1>1261)                      →  CGGCCTACCGGGAGCAAACGGGGCAGAAAGAAACTCCTGTATATATTCAAACAACCATTTATGA
A03-Y92833-C473FED150-2-2-SEQ1.ab1 (1>843)   →  CGGCCTACCGGGAGCAAACGGGGCAGAAAGAAACTCCTGTATATATTCAAACAACCATTTATGA 940       950       960       970       980       990
                |    |    |    |    |    |    |    |    |    |    |    |
      GACCAGTACAAACTACTCAAGAGGAAGATGGCTGTAGCTGCCGATTTCCAGAAGAAGAAGAA C473FED150-2.seq(1>1261)                      →  GACCAGTACAAACTACTCAAGAGGAAGATGGCTGTAGCTGCCGATTTCCAGAAGAAGAAGAA
A03-Y92833-C473FED150-2-2-SEQ1.ab1 (1>843)   →  GACCAGTACAAACTACTCAAGAGGAAGATGGCTGTAGCTGCCGATTTCCAGAAGAAGAAGAA
```

FIG. 3 (Cont.)

```
                    1000      1010      1020      1030      1040      1050
C473FED150-2.seq(1>1261)
                    GGAGGATGTGAACTGAGAGTGAAGTTCAGCAGGAGGGGCAGACGGCCCCGCGGTACAAGCAGGG
A03-Y92833-C473FED150-2-2-SEQ1.ab1 (1>843)
                    GGAGGATGTGAACTGAGAGTGAAGTTCAGCAGGAGGGGCAGACGGCCCCGCGGTACAAGCAGGG
                    GGAGGATGTGAACTGAGAGTGAAGTTCAGCAGGAGGGGCAGACGGCCCCGCGGTACAAGCAGGG 1060      1070      1080      1090      1100      1110
C473FED150-2.seq(1>1261)
                    CCAGAACCAGCTCTATAACGAGCTCAATCTAGGACGAAGAGAGGAGTACGATGTTTTGGGACA
A03-Y92833-C473FED150-2-2-SEQ1.ab1 (1>843)
                    CCAGAACCAGCTCTATAACGAGCTCAATCTAGGACGAAGAGAGGAGTACGATGTTTTGGGACA
                    CCAGAACCAGCTCTATAACGAGCTCAATCTAGGACGAAGAGAGGAGTACGATGTTTTGGGACA 1120      1130      1140      1150      1160      1170
C473FED150-2.seq(1>1261)
                    AGAGACGTGGCCGGGACCCTGAGATGGGGGAAAGCCGAGAAGGAAGAACCCTCAGGAAGGC
A03-Y92833-C473FED150-2-2-SEQ1.ab1 (1>843)
                    AGAGACGTGGCCGGGACCCTGAGATGGGGGAAAGCCGAGAAGGAAGAACCCTCAGGAAGGC
A04-Y92833-C473FED150-2-2-SEQ2.ab1 (1>837)
                    GGGGGGAaAGCCGAGAAGGAAGAACCCTCAGGAAGGC 1180      1190      1200      1210      1220      1230      1240
C473FED150-2.seq(1>1261)
                    CTGTACAATGAACTGCAGAAAGATAAGATGGCGGAGGCCTACAGTGAGATTGGGATGAAAGG
A03-Y92833-C473FED150-2-2-SEQ1.ab1 (1>843)
                    CTGTACAATGAACTGCAGAAAGATAAGATGGCGGAGGCCTACAGTGAGATTGGGATGAAAGG
A04-Y92833-C473FED150-2-2-SEQ2.ab1 (1>837)
                    CTGTACAATGAACTGCAGAAAGATAAGATGGCGGAGGCCTACAGTGAGATTGGGATGAAAGG 1250      1260      1270      1280      1290      1300
C473FED150-2.seq(1>1261)
                    CGAGCGCCGGAGGGGCAAGGGGCACGATGGCCTTTACCAGGGTCTCAGTACAGCCACCAAGG
A03-Y92833-C473FED150-2-2-SEQ1.ab1 (1>843)
                    CGAGCGCCGGAGGGGCAAGGGGCACGATGGCCTTTACCAGGGTCTCAGTACAGCCACCAAGG
A04-Y92833-C473FED150-2-2-SEQ2.ab1 (1>837)
                    CGAGCGCCGGAGGGGCAAGGGGCACGATGGCCTTTACCAGGGTCTCAGTACAGCCACCAAGG
```

*FIG. 3 (Cont.)*

```
           1310      1320      1330      1340      1350      1360
           ACACCTACGACGAGCCCTTCACATGCGAGCCCTGCCCCCTCGGCTAACGCGCCGGCCCCACGACCCG

C473FED150-2.seq(1>1261)
A03-Y92833-C473FED150-2-2-SEQ1.ab1 (1>843)        ↑  ↑  ↑
A04-Y92833-C473FED150-2-2-SEQ2.ab1 (1>837)
           ACACCTACGACGAGCCCTTCACATGCGAGCCCTGCCCCCTGCCCCCTCGGCTAA
           ACACCTACGACGCGCCCTTC
           ACACCTACGACGAGCCCTTCACATGCGAGCCCTGCCCCCTGCCCCCTCGGCTAACGCGCCGGCCCCACGACCCG 1370      1380      1390      1400      1410      1420
           CAGCGCCCGACCGGAAAGGAGCGCACGACCGACCCCATGGCATCGGATAAAATAAAAGATTTTATTTAG A04-Y92833-C473FED150-2-2-SEQ2.ab1 (1>837)        ↑
           CAGCGCCCGACCGGAAAGGAGCGCACGACCGACCCCATGGCATCGGATAAAATAAAAGATTTTATTTAG 1430      1440      1450      1460      1470      1480
           TCTCCAGAAAAAGGGGGAATGAAAGACCCCACCTGTAGGTTTGGCAAGCTAGCTTAAGTAA A04-Y92833-C473FED150-2-2-SEQ2.ab1 (1>837)        ↑
           TCTCCAGAAAAAGGGGGAATGAAAGACCCCACCTGTAGGTTTGGCAAGCTAGCTTAAGTAA 1490    1500    1510    1520    1530    1540    1550
           CGGCCATTTTGGCAAGGCATGGAAAATACATAACTGAGAATAGAGAAGTTCAGATCAAGGTTAG A04-Y92833-C473FED150-2-2-SEQ2.ab1 (1>837)        ↑
           CGGCCATTTTGGCAAGGCATGGAAAATACATAACTGAGAATAGAGAAGTTCAGATCAAGGTTAG 1560      1570      1580      1590      1600      1610
           GAACAGAGAGCAGCAGAATATGGGCCAAACAGGATATCTGTGGTAAGGCAGTTCCTGCCCCG A04-Y92833-C473FED150-2-2-SEQ2.ab1 (1>837)        ↑
           GAACAGAGAGCAGCAGAATATGGGCCAAACAGGATATCTGTGGTAAGGCAGTTCCTGCCCCG 1620      1630      1640      1650      1660      1670
           GCTCAGGGCCAAGAACAGATGGTCCCCGCCCTCAGCAGTTCTAGAGAAC A04-Y92833-C473FED150-2-2-SEQ2.ab1 (1>837)        ↑
           GCTCAGGGCCAAGAACAGATGGTCCCCGCCCTCAGCAGTTCTAGAGAAC
```

*FIG. 3 (Cont.)*

```
                          1680      1690      1700      1710      1720      1730
                          CATCAGATGTTTCCAGGGTGCCCCAAGGACCTGAAATGACCCTGTGCCTTATTTGAACTAAC
A04-Y92833-C473FED150-2-2-SEQ2.ab1 (1>837)
                       →  CATCAGATGTTTCCAGGGTGCCCCAAGGACCTGAAATGACCCTGTGCCTTATTTGAACTAAC 1740      1750      1760      1770      1780      1790
                          CAATCAGTTCGGCTTCTCGCTTCGCGCGGCTTCTGCTCCCCGAGCTCAATAAAAGAGCC
A04-Y92833-C473FED150-2-2-SEQ2.ab1 (1>837)
                       →  CAATCAGTTCGGCTTCTCGCTTCGCGCGGCTTCTGCTCCCCGAGCTCAATAAAAGAGCC 1800      1810      1820      1830      1840      1850      1860
                          CACAACCCCTCACTCGGCGGCCAGTCCTCCGATAGACTGGCTCGCCCGGGTACCCGTGTAT
A04-Y92833-C473FED150-2-2-SEQ2.ab1 (1>837)
                       →  CACAACCCCTCACTCGGCGGCCAGTCCTCCGATAGACTGGCTCGCCCGGGTACCCGTGTAT 1870      1880      1890      1900      1910      1920
                          CCAATAAACCCTCTTGCAGTTGCATCCGACTTGTGGTCTCGCTGTTCCTTGgGAGGGTCTCC
A04-Y92833-C473FED150-2-2-SEQ2.ab1 (1>837)
                       →  CCAATAAACCCTCTTGCAGTTGCATCCGACTTGTGGTCTCGCTGTTCCTTGgGAGGGTCTCC 1930      1940      1950      1960      1970
                          TCTGAGTGATTGACTACCCGTCAGCGGGGGTCTTTCATGGGTAACAGTTTCTTGAA
A04-Y92833-C473FED150-2-2-SEQ2.ab1 (1>837)
                       →  TCTGAGTGATTGACTACCCGTCAGCGGGGGTCTTTCATGGGTAACAGTTTCTTGAA
```

FIG. 3 (Cont.)

| Lot No. | N.A. | | Cloning Vector | pCDH-EF1a-AT-Free |
|---|---|---|---|---|
| Cloning Sites | EcoRI / XbaI | | Insert Size | 1272 bp |
| QC Results | | | | |
| Test Items | Specifications | | | Results |
| Insert Sequence | Insert sequence results consistent with target | | | Pass |
| Vector Sequence | Flanking sequence consistent with expected | | | N/A |
| ORF Across Junction | Correct and consistent with target | | | N/A |
| Restriction Digest | Expected fragment sizes observed | | | N/A |
| PCR Amplification | Correct without non - specific bands | | | Pass |
| DNA Quantity/Quality | Actual yield (by A 260) | | | 10 µg/tube |
| | Concentration (n/a if lyophilized) | | | 200 ng/µL |
| | Purity (A 260/A280 = 1.8 – 2.0) | | | Pass |
| | # of Tubes | | | 1 |
| | Matrix | | | TE (lyophilized) |
| Endotoxin Test | Verified, <0.1 EU/µg (Endo-Free Preps Only) | | | N/A |
| Appearance | Clear, no visible particles | | | Pass |
| Label | Correct and white | | | Pass |
| Restriction Digestion Map | | | | |

Lane 1:

Plasmid

Lane 2:

Plasmid digested with ClaI / KpnI

Lane M:

DNA Marker

*FIG. 5*

```
                          10        20        30        40        50
E10-S88031-C9721EF200-1-chu01-seqF.ab1 (1>817)
  →    TGGGTGGAGACTGAAGTTAGGCCAGCTTGGCACTTGTGATGTAATTCTCCTTGGAATTTGC
       TGGGTGGAGACTGAAGTTAGGCCAGCTTGGCACTTGTGATGTAATTCTCCTTGGAATTTGC 60        70        80        90       100       110
E10-S88031-C9721EF200-1-chu01-seqF.ab1 (1>817)
  →    CCTTTTTGAGTTTGGATCTTGGTTCATTCTCAAGCCTCAGACACAGTGGTTCAAAAGTTTT
       CCTTTTTGAGTTTGGATCTTGGTTCATTCTCAAGCCTCAGACACAGTGGTTCAAAAGTTTT 120       130       140       150       160       170
E10-S88031-C9721EF200-1-chu01-seqF.ab1 (1>817)
  →    TTCTTCCATTTCAGGTGTCGTGATTCGAATTCGGCCACCATGTACCGGATGGCAGCTGCTG
  →    TTCTTCCATTTCAGGTGTCGTGATTCGAATTCGGCCACCATGTACCGGATGGCAGCTGCTG
C9721EF200-1.seq(1>1273)
                       GAATTCGGCCACCATGTACCGGATGGCAGCTGCTG 180       190       200       210       220       230
E10-S88031-C9721EF200-1-chu01-seqF.ab1 (1>817)
  →    AGCTGTATCGGCCCTGTCTCTGGCCCTGGTCACAAATAGCGGCCCCTACCAGCAGCAGCAC
  →    AGCTGTATCGGCCCTGTCTCTGGCCCTGGTCACAAATAGCGGCCCCTACCAGCAGCAGCAC
C9721EF200-1.seq(1>1273)
       AGCTGTATCGGCCCTGTCTCTGGCCCTGGTCACAAATAGCGGCCCCTACCAGCAGCAGCAC 240       250       260       270       280       290
E10-S88031-C9721EF200-1-chu01-seqF.ab1 (1>817)
  →    CAAGAAAACACAGCTGCAACTGGAACACCTCCTGCTGGACCTGCAGATGATCCTGAACG
  →    CAAGAAAACACAGCTGCAACTGGAACACCTCCTGCTGGACCTGCAGATGATCCTGAACG
C9721EF200-1.seq(1>1273)

300       310       320       330       340       350
E10-S88031-C9721EF200-1-chu01-seqF.ab1 (1>817)
  →    GCATCAACAACTACAAGAACCCAAGCTGACCCGGATGCTGACCTTCAAGTTCTACATG
  →    GCATCAACAACTACAAGAACCCAAGCTGACCCGGATGCTGACCTTCAAGTTCTACATG
C9721EF200-1.seq(1>1273)
```

*FIG. 6*

```
                              360       370       380       390       400       410
                              CCCAAGAAGGGCCACCGAGCTGAAGCTGAAGCACCTCCAGTGCCTGGAAGAGAGGAACTGAAGCCCCT

E10-S88031-C9721EF200-1-chu01-seqF.ab1 (1>817)  → CCCAAGAAGGGCCACCGAGCTGAAGCTGAAGCACCTCCAGTGCCTGGAAGAGAGGAACTGAAGCCCCT
C9721EF200-1.seq(1>1273)                         → CCCAAGAAGGGCCACCGAGCTGAAGCTGAAGCACCTCCAGTGCCTGGAAGAGAGGAACTGAAGCCCCT 420       430       440       450       460       470
                              GGAAGAAGTGCTGAATCTGGCCCAGAGCAAGAACTTCCACCTGAGGCCTAGGGACCTGA E10-S88031-C9721EF200-1-chu01-seqF.ab1 (1>817)  → GGAAGAAGTGCTGAATCTGGCCCAGAGCAAGAACTTCCACCTGAGGCCTAGGGACCTGA
C9721EF200-1.seq(1>1273)                         → GGAAGAAGTGCTGAATCTGGCCCAGAGCAAGAACTTCCACCTGAGGCCTAGGGACCTGA 480       490       500       510       520       530
                              TCAGCAACATCAACGTGATCGTGCTGCTGGAACTGAAAGGCAGCGAGACAACCTTCATGTGC E10-S88031-C9721EF200-1-chu01-seqF.ab1 (1>817)  → TCAGCAACATCAACGTGATCGTGCTGCTGGAACTGAAAGGCAGCGAGACAACCTTCATGTGC
C9721EF200-1.seq(1>1273)                         → TCAGCAACATCAACGTGATCGTGCTGCTGGAACTGAAAGGCAGCGAGACAACCTTCATGTGC 540       550       560       570       580       590
                              GAGTACGGCCGAGCGAGAGAGCAGGTACCATCGTGGAATTTCTGAACCGGTGGATCACCTTCTG E10-S88031-C9721EF200-1-chu01-seqF.ab1 (1>817)  → GAGTACGGCCGAGCGAGAGAGCAGGTACCATCGTGGAATTTCTGAACCGGTGGATCACCTTCTG
C9721EF200-1.seq(1>1273)                         → GAGTACGGCCGAGCGAGAGAGCAGGTACCATCGTGGAATTTCTGAACCGGTGGATCACCTTCTG 600       610       620       630       640
                              CCAGAGCATCATCAGCACCCTGACCACGCCGAGCGGCCGAGCGGCCGACCACCAACACGGG E10-S88031-C9721EF200-1-chu01-seqF.ab1 (1>817)  → CCAGAGCATCATCAGCACCCTGACCACGCCGAGCGGCCGAGCGGCCGACCACCAACACGGG
C9721EF200-1.seq(1>1273)                         → CCAGAGCATCATCAGCACCCTGACCACGCCGAGCGGCCGAGCGGCCGACCACCAACACGGG
E11-S88031-C9721EF200-1-1-SEQ1.ab1 (1>828)       →                         CACGACGCGCagCGCGCGCGACCACCAACACGGG 650       660       670       680       690       700
                              CGCCCACCATCGGTCGGCAGCCCCGTCCCTGCGCCCAGAAGCGTGCCGGCCAGCGGCG E10-S88031-C9721EF200-1-chu01-seqF.ab1 (1>817)  → CGCCCACCATCGGTCGGCAGCCCCGTCCCTGCGCCCAGAAGCGTGCCGGCCAGCGGCG
C9721EF200-1.seq(1>1273)                         → CGCCCACCATCGGTCGGCAGCCCCGTCCCTGCGCCCAGAAGCGTGCCGGCCAGCGGCG
E11-S88031-C9721EF200-1-1-SEQ1.ab1 (1>828)       → CGCCCACCATCGGTCGGCAGCCCCGTCCCTGCGCCCAGAAGCGTGCCGGCCAGCGGCG
```

*FIG. 6 (Cont.)*

```
                710       720       730       740       750       760
                GGGGGCGCAGTGCACACGAGGGGCTGGACTTCGCCTGTGATATCTACATTTGGGCCCC
E10-S88031-C9721EF200-1-chu01-seqF.ab1 (1>817)  →  GGGGGCGCAGTGCACACGAGGGGGCTGGACTTCGCCTGTGATATCTACATTTGGGCCCC
C9721EF200-1.seq(1>1273)                         →  GGGGGCGCAGTGCACACGAGGGGGCTGGACTTCGCCTGTGATATCTACATTTGGGCCCC
E11-S88031-C9721EF200-1-1-SEQ1.ab1 (1>828)       →  GGGGGCGCAGTGCACACGAGGGGGCTGGACTTCGCCTGTGATATCTACATTTGGGCCCC 770       780       790       800       810       820
                TCTGGCTGGTACTTGCGGGGTCCTGCTTTCACTCGTGATCACTCTT
E10-S88031-C9721EF200-1-chu01-seqF.ab1 (1>817)  →  TCTGGCTGGTACTTGCGGGGTCCTGCTTTCACTCGTGATCACTCTT
C9721EF200-1.seq(1>1273)                         →  TCTGGCTGGTACTTGCGGGGTCCTGCTTTCACTCGTGATCACTCTTTACTGTAGGA
E11-S88031-C9721EF200-1-1-SEQ1.ab1 (1>828)       →  TCTGGCTGGTACTTGCGGGGTCCTGCTTTCACTCGTGATCACTCTTTACTGTAGGA 830       840       850       860       870       880
C9721EF200-1.seq(1>1273)                         →  GCAAGCGGAGCAGACTGCTGCACAGCGACTACATGAACATGACCCCCGGAGGCCTGGC
E11-S88031-C9721EF200-1-1-SEQ1.ab1 (1>828)       →  GCAAGCGGAGCAGACTGCTGCACAGCGACTACATGAACATGACCCCCGGAGGCCTGGC 890       900       910       920       930       940
C9721EF200-1.seq(1>1273)                         →  CCCACCCGGAAGCACTACCAGCCCTCCCAGGGATTTCGCGCGCCTACCGGGAG
E11-S88031-C9721EF200-1-1-SEQ1.ab1 (1>828)       →  CCCACCCGGAAGCACTACCAGCCCTCCCAGGGATTTCGCGCGCCTACCGGGAG 950       960       970       980       990      1000
C9721EF200-1.seq(1>1273)                         →  CAAACGGGGCAGAAAGAAACTCCTGTATATATTCAAACAACCATTTATGAGACCAGTAC
E11-S88031-C9721EF200-1-1-SEQ1.ab1 (1>828)       →  CAAACGGGGCAGAAAGAAACTCCTGTATATATTCAAACAACCATTTATGAGACCAGTAC
```

AAACTACTCAAGAGGAAGAATGGCTGTGTAGCTGTGTAGCTGTGCCGATTTCCAGAAGAAGAAGAAGAAGGAGGA

C9721EF200-1.seq(1>1273)
E11-S88031-C9721EF200-1-1-SEQ1.ab1 (1>828)

1070    1080    1090    1100    1110    1120

AAACTACTCAAGAGGAAGAATGGCTGTGTAGCTGTGTAGCTGTGCCGATTTCCAGAAGAAGAAGAAGAAGGAGGA
AAACTACTCAAGAGGAAGAATGGCTGTGTAGCTGTGTAGCTGTGCCGATTTCCAGAAGAAGAAGAAGAAGGAGGA

TGTGAACTGAGAGTGAAGTTCAGCAGGAGCGGCAGACGCCCCGCCGGTACAAGCAGGGCCA

C9721EF200-1.seq(1>1273)
E11-S88031-C9721EF200-1-1-SEQ1.ab1 (1>828)

1130    1140    1150    1160    1170    1180

TGTGAACTGAGAGTGAAGTTCAGCAGGAGCGGCAGACGCGCGCCCCGCCGGTACAAGCAGGGCCA
TGTGAACTGAGAGTGAAGTTCAGCAGGAGCGGCAGACGCGCGCCCCGCCGGTACAAGCAGGGCCA

GAACCAGGCTCTATAACGAGCTCAATCTAGGACGAAGAGAGAGGAGTACGATGTGTTTGGACA

C9721EF200-1.seq(1>1273)
E11-S88031-C9721EF200-1-1-SEQ1.ab1 (1>828)

1190    1200    1210    1220    1230

GAACCAGGCTCTATAACGAGCTCAATCTAGGACGAAGAGAGAGGAGTACGATGTGTTTGGACA
GAACCAGGCTCTATAACGAGCTCAATCTAGGACGAAGAGAGAGGAGTACGATGTGTTTGGACA

AGAGACGTGGCCGGGACCCTGAGATGGGGGGAAAGCCGAGAAGGAAGAACCCTCAGGAA

C9721EF200-1.seq(1>1273)
E11-S88031-C9721EF200-1-1-SEQ1.ab1 (1>828)

1240    1250    1260    1270    1280    1290

AGAGACGTGGCCGGGACCCTGAGATGGGGGGAAAGCCGAGAAGGAAGAACCCTCAGGAA
AGAGACGTGGCCGGGACCCTGAGATGGGGGGAAAGCCGAGAAGGAAGAACCCTCAGGAA

GGCCTGTACAATGAACTGCAGAAAGATAAGATGGCGAGGCCTACAGTGAGATTGGGAT

C9721EF200-1.seq(1>1273)
E11-S88031-C9721EF200-1-1-SEQ1.ab1 (1>828)

1300    1310    1320    1330    1340    1350

GGCCTGTACAATGAACTGCAGAAAGATAAGATGGCGGAGGCCTACAGTGAGATTGGGAT
GGCCTGTACAATGAACTGCAGAAAGATAAGATGGCGGAGGCCTACAGTGAGATTGGGAT

GAAAGGCGAGCGCGCCGGAGGGGCAAGGGCCACGATGGCCTTTACCAGGGTCTCAGTACAG

C9721EF200-1.seq(1>1273)
E11-S88031-C9721EF200-1-1-SEQ1.ab1 (1>828)

GAAAGGCGAGCGCGCCGGAGGGGCAAGGGCCACGATGGCCTTTACCAGGGTCTCAGTACAG
GAAAGGCGAGCGCGCCGGAGGGGCAAGGGCCACGATGGCCTTTACCAGGGTCTCAGTACAG

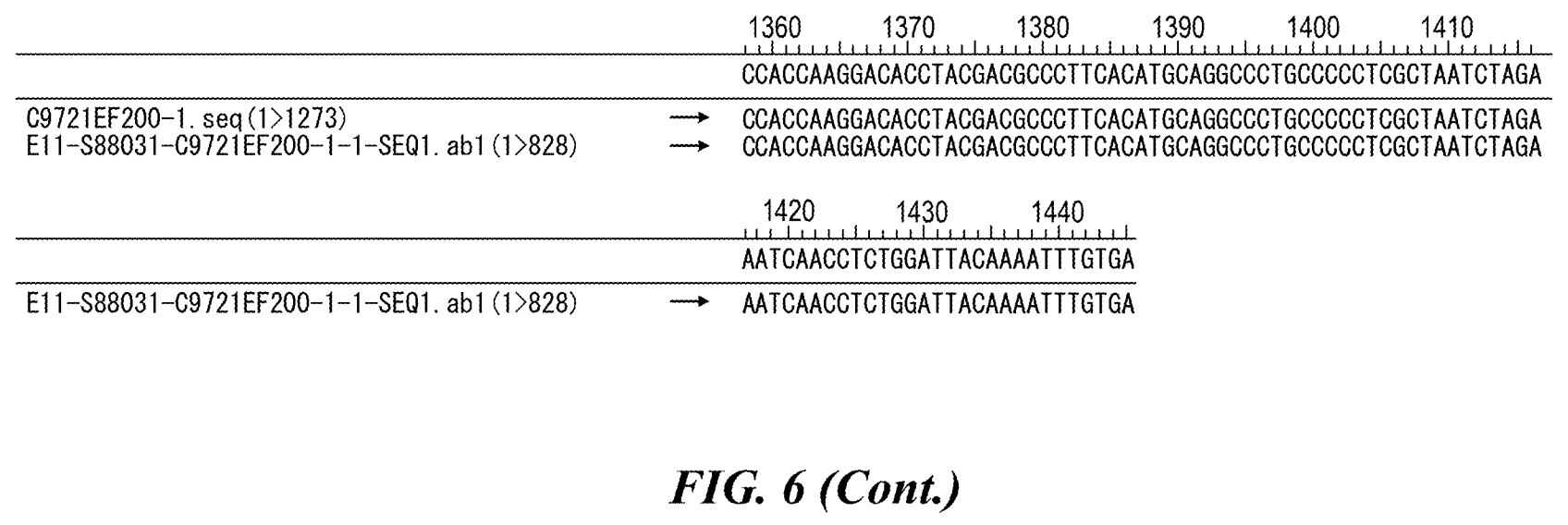

CCACCAAGGACACCTACGACGCCCTTCACATGCAGGCCCTGCCCCCTCGCTAATCTAGA

C9721EF200-1.seq(1>1273)
CCACCAAGGACACCTACGACGCCCTTCACATGCAGGCCCTGCCCCCTCGCTAATCTAGA
E11-S88031-C9721EF200-1-1-SEQ1.ab1 (1>828)
CCACCAAGGACACCTACGACGCCCTTCACATGCAGGCCCTGCCCCCTCGCTAATCTAGA 1420      1430      1440

AATCAACCTCTGGATTACAAAAATTTGTGA

E11-S88031-C9721EF200-1-1-SEQ1.ab1 (1>828)
AATCAACCTCTGGATTACAAAAATTTGTGA

*FIG. 6 (Cont.)*

FIG. 7
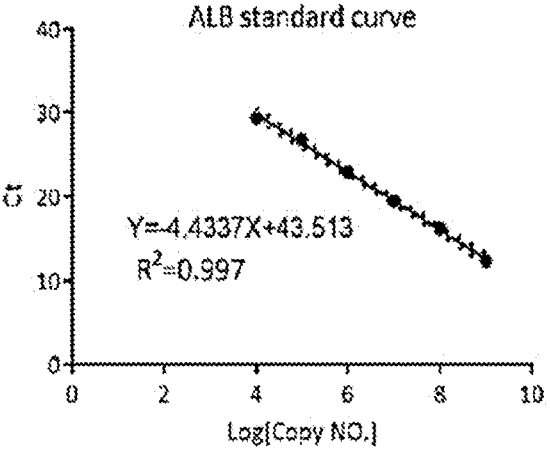
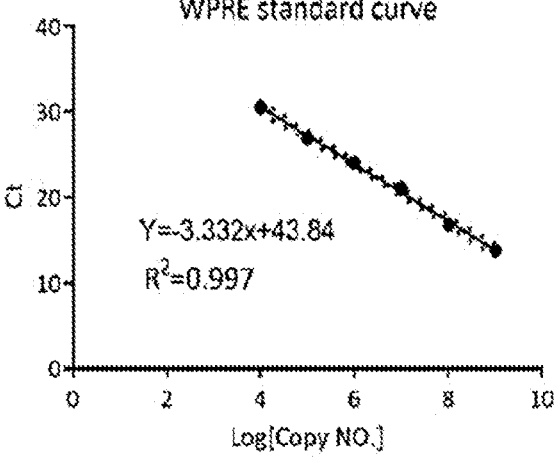

FIG. 8
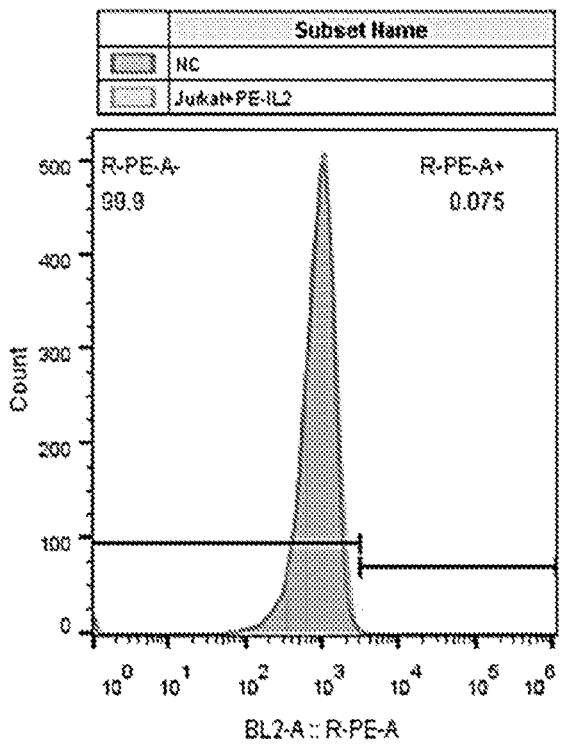
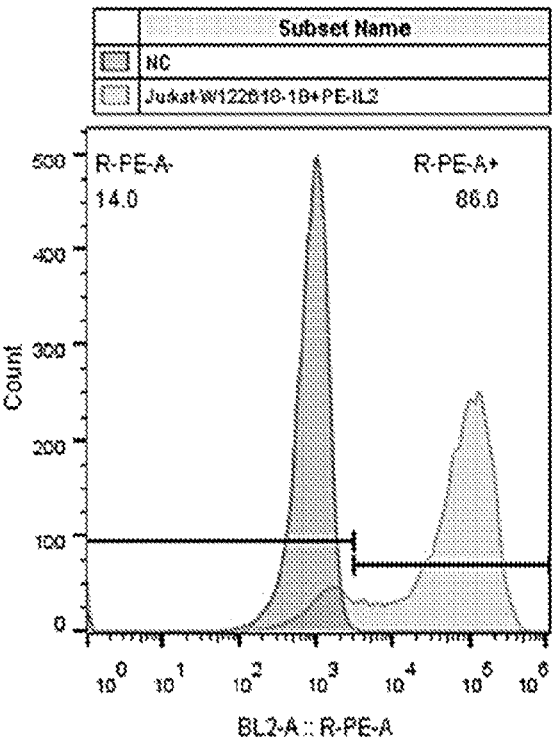

SEQUENCE LISTING

<160> NUMBER OF SEQ ID NOS: 25

<210> SEQ ID NO 1
<211> LENGTH: 12
<212> TYPE: PRT
<213> ORGANISM: Homo sapiens

<400> SEQUENCE: 1

Glu Pro Lys Ser Cys Asp Lys Thr His Thr Cys Pro
1               5                   10

<210> SEQ ID NO 2
<211> LENGTH: 12
<212> TYPE: PRT
<213> ORGANISM: Homo sapiens

<400> SEQUENCE: 2

Glu Arg Lys Cys Cys Val Glu Cys Pro Pro Cys Pro
1               5                   10

-continued

```
<210> SEQ ID NO 3
<211> LENGTH: 12
<212> TYPE: PRT
<213> ORGANISM: Homo sapiens

<400> SEQUENCE: 3

Glu Ser Lys Tyr Gly Pro Pro Cys Pro Ser Cys Pro
1               5               10

<210> SEQ ID NO 4
<211> LENGTH: 161
<212> TYPE: PRT
<213> ORGANISM: Homo sapiens

<400> SEQUENCE: 4

Ser Gln Phe Arg Val Ser Pro Leu Asp Arg Thr Trp Asn Leu Gly Glu
1               5               10              15

Thr Val Glu Leu Lys Cys Gln Val Leu Leu Ser Asn Pro Thr Ser Gly
                20              25              30

Cys Ser Trp Leu Phe Gln Pro Arg Gly Ala Ala Ala Ser Pro Thr Phe
            35              40              45

Leu Leu Tyr Leu Ser Gln Asn Lys Pro Lys Ala Ala Glu Gly Leu Asp
        50              55              60

Thr Gln Arg Phe Ser Gly Lys Arg Leu Gly Asp Thr Phe Val Leu Thr
65              70              75              80

Leu Ser Asp Phe Arg Arg Glu Asn Glu Gly Tyr Tyr Phe Cys Ser Ala
                85              90              95

Leu Ser Asn Ser Ile Met Tyr Phe Ser His Phe Val Pro Val Phe Leu
                100             105             110

Pro Ala Lys Pro Thr Thr Thr Pro Ala Pro Arg Pro Pro Thr Pro Ala
            115             120             125

Pro Thr Ile Ala Ser Gln Pro Leu Ser Leu Arg Pro Glu Ala Cys Arg
        130             135             140

Pro Ala Ala Gly Gly Ala Val His Thr Arg Gly Leu Asp Phe Ala Cys
145             150             155             160

Asp

<210> SEQ ID NO 5
<211> LENGTH: 149
<212> TYPE: PRT
<213> ORGANISM: Homo sapiens

<400> SEQUENCE: 5

Leu Gln Gln Thr Pro Ala Tyr Ile Lys Val Gln Thr Asn Lys Met Val
1               5               10              15

Met Leu Ser Cys Glu Ala Lys Ile Ser Leu Ser Asn Met Arg Ile Tyr
                20              25              30

Trp Leu Arg Gln Arg Gln Ala Pro Ser Ser Asp Ser His His Glu Phe
            35              40              45

Leu Ala Leu Trp Asp Ser Ala Lys Gly Thr Ile His Gly Glu Glu Val
        50              55              60

Glu Gln Glu Lys Ile Ala Val Phe Arg Asp Ala Ser Arg Phe Ile Leu
65              70              75              80

Asn Leu Thr Ser Val Lys Pro Glu Asp Ser Gly Ile Tyr Phe Cys Met
                85              90              95

Ile Val Gly Ser Pro Glu Leu Thr Phe Gly Lys Gly Thr Gln Leu Ser
                100             105             110
```

Val Val Asp Phe Leu Pro Thr Thr Ala Gln Pro Thr Lys Lys Ser Thr
    115                 120                 125

Leu Lys Lys Arg Val Cys Arg Leu Pro Arg Pro Glu Thr Gln Lys Gly
    130                 135                 140

Pro Leu Cys Ser Pro
145

<210> SEQ ID NO 6
<211> LENGTH: 134
<212> TYPE: PRT
<213> ORGANISM: Homo sapiens

<400> SEQUENCE: 6

Asn Lys Ile Leu Val Lys Gln Ser Pro Met Leu Val Ala Tyr Asp Asn
1               5                   10                  15

Ala Val Asn Leu Ser Cys Lys Tyr Ser Tyr Asn Leu Phe Ser Arg Glu
            20                  25                  30

Phe Arg Ala Ser Leu His Lys Gly Leu Asp Ser Ala Val Glu Val Cys
        35                  40                  45

Val Val Tyr Gly Asn Tyr Ser Gln Gln Leu Gln Val Tyr Ser Lys Thr
    50                  55                  60

Gly Phe Asn Cys Asp Gly Lys Leu Gly Asn Glu Ser Val Thr Phe Tyr
65                  70                  75                  80

Leu Gln Asn Leu Tyr Val Asn Gln Thr Asp Ile Tyr Phe Cys Lys Ile
                85                  90                  95

Glu Val Met Tyr Pro Pro Pro Tyr Leu Asp Asn Glu Lys Ser Asn Gly
            100                 105                 110

Thr Ile Ile His Val Lys Gly Lys His Leu Cys Pro Ser Pro Leu Phe
        115                 120                 125

Pro Gly Pro Ser Lys Pro
    130

<210> SEQ ID NO 7
<211> LENGTH: 21
<212> TYPE: PRT
<213> ORGANISM: Homo sapiens

<400> SEQUENCE: 7

Gly Ile Ile Val Thr Asp Val Ile Ala Thr Leu Leu Leu Ala Leu Gly
1               5                   10                  15

Val Phe Cys Phe Ala
            20

<210> SEQ ID NO 8
<211> LENGTH: 26
<212> TYPE: PRT
<213> ORGANISM: Homo sapiens

<400> SEQUENCE: 8

Val Met Ser Val Ala Thr Ile Val Ile Val Asp Ile Cys Ile Thr Gly
1               5                   10                  15

Gly Leu Leu Leu Leu Val Tyr Tyr Trp Ser
            20                  25

<210> SEQ ID NO 9
<211> LENGTH: 21
<212> TYPE: PRT
<213> ORGANISM: Homo sapiens

<400> SEQUENCE: 9

-continued

```
Gly Phe Leu Phe Ala Glu Ile Val Ser Ile Phe Val Leu Ala Val Gly
1               5                   10                  15

Val Tyr Phe Ile Ala
            20

<210> SEQ ID NO 10
<211> LENGTH: 21
<212> TYPE: PRT
<213> ORGANISM: Homo sapiens

<400> SEQUENCE: 10

Leu Cys Tyr Leu Leu Asp Gly Ile Leu Phe Ile Tyr Gly Val Ile Leu
1               5                   10                  15

Thr Ala Leu Phe Leu
            20

<210> SEQ ID NO 11
<211> LENGTH: 27
<212> TYPE: PRT
<213> ORGANISM: Homo sapiens

<400> SEQUENCE: 11

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 12
<211> LENGTH: 21
<212> TYPE: PRT
<213> ORGANISM: Homo sapiens

<400> SEQUENCE: 12

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 13
<211> LENGTH: 21
<212> TYPE: PRT
<213> ORGANISM: Homo sapiens

<400> SEQUENCE: 13

Ile Thr Leu Gly Leu Leu Val Ala Gly Val Leu Val Leu Leu Val Ser
1               5                   10                  15

Leu Gly Val Ala Ile
            20

<210> SEQ ID NO 14
<211> LENGTH: 113
<212> TYPE: PRT
<213> ORGANISM: Homo sapiens

<400> SEQUENCE: 14

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
            35                  40                  45
```

-continued

```
Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
                100                 105                 110

Arg

<210> SEQ ID NO 15
<211> LENGTH: 41
<212> TYPE: PRT
<213> ORGANISM: Homo sapiens

<400> SEQUENCE: 15

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
                20                  25                  30

Pro Arg Asp Phe Ala Ala Tyr Arg Ser
        35                  40

<210> SEQ ID NO 16
<211> LENGTH: 38
<212> TYPE: PRT
<213> ORGANISM: Homo sapiens

<400> SEQUENCE: 16

Cys Trp Leu Thr Lys Lys Lys Tyr Ser Ser Ser Val His Asp Pro Asn
1               5                   10                  15

Gly Glu Tyr Met Phe Met Arg Ala Val Asn Thr Ala Lys Lys Ser Arg
                20                  25                  30

Leu Thr Asp Val Thr Leu
        35

<210> SEQ ID NO 17
<211> LENGTH: 42
<212> TYPE: PRT
<213> ORGANISM: Homo sapiens

<400> SEQUENCE: 17

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
        35                  40

<210> SEQ ID NO 18
<211> LENGTH: 42
<212> TYPE: PRT
<213> ORGANISM: Homo sapiens

<400> SEQUENCE: 18

Ala Leu Tyr Leu Leu Arg Arg Asp Gln Arg Leu Pro Pro Asp Ala His
1               5                   10                  15

Lys Pro Pro Gly Gly Gly Ser Phe Arg Thr Pro Ile Gln Glu Glu Gln
                20                  25                  30
```

```
Ala Asp Ala His Ser Thr Leu Ala Lys Ile
        35                  40
```

```
<210> SEQ ID NO 19
<211> LENGTH: 48
<212> TYPE: PRT
<213> ORGANISM: Homo sapiens

<400> SEQUENCE: 19
```

```
Gln Arg Arg Lys Tyr Arg Ser Asn Lys Gly Glu Ser Pro Val Glu Pro
1                5                10                  15

Ala Glu Pro Cys His Tyr Ser Cys Pro Arg Glu Glu Glu Gly Ser Thr
            20                  25                  30

Ile Pro Ile Gln Glu Asp Tyr Arg Lys Pro Glu Pro Ala Cys Ser Pro
        35                  40                  45
```

```
<210> SEQ ID NO 20
<211> LENGTH: 69
<212> TYPE: PRT
<213> ORGANISM: Artificial Sequence
<220> FEATURE:
<223> OTHER INFORMATION: (CD8H)-(CD8TM)
<220> FEATURE:
<221> NAME/KEY: MISC_FEATURE
<222> LOCATION: (1)..(45)
<223> OTHER INFORMATION: CD8H
<220> FEATURE:
<221> NAME/KEY: MISC_FEATURE
<222> LOCATION: (46)..(69)
<223> OTHER INFORMATION: CD8TM

<400> SEQUENCE: 20
```

```
Thr Thr Thr Pro Ala Pro Arg Pro Pro Thr Pro Ala Pro Thr Ile Ala
1                5                10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys
65
```

```
<210> SEQ ID NO 21
<211> LENGTH: 153
<212> TYPE: PRT
<213> ORGANISM: Homo sapiens

<400> SEQUENCE: 21
```

```
Met Tyr Arg Met Gln Leu Leu Ser Cys Ile Ala Leu Ser Leu Ala Leu
1                5                10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95
```

-continued

```
Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
            115                 120                 125

Asp Glu Thr Ala Thr Ile Val Glu Phe Leu Asn Arg Trp Ile Thr Phe
        130                 135                 140

Cys Gln Ser Ile Ile Ser Thr Leu Thr
145                 150
```

```
<210> SEQ ID NO 22
<211> LENGTH: 417
<212> TYPE: PRT
<213> ORGANISM: Artificial Sequence
<220> FEATURE:
<223> OTHER INFORMATION: CD25-CAR 4
<220> FEATURE:
<221> NAME/KEY: MISC_FEATURE
<222> LOCATION: (1)..(153)
<223> OTHER INFORMATION: IL-2 receptor ligand
<220> FEATURE:
<221> NAME/KEY: MISC_FEATURE
<222> LOCATION: (154)..(198)
<223> OTHER INFORMATION: CD8h
<220> FEATURE:
<221> NAME/KEY: MISC_FEATURE
<222> LOCATION: (199)..(222)
<223> OTHER INFORMATION: CD8a TMD
<220> FEATURE:
<221> NAME/KEY: MISC_FEATURE
<222> LOCATION: (223)..(263)
<223> OTHER INFORMATION: CD28CD
<220> FEATURE:
<221> NAME/KEY: MISC_FEATURE
<222> LOCATION: (264)..(305)
<223> OTHER INFORMATION: 4-1BB/CD137CD
<220> FEATURE:
<221> NAME/KEY: MISC_FEATURE
<222> LOCATION: (305)..(417)
<223> OTHER INFORMATION: CD3zeta
```

```
<400> SEQUENCE: 22

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
        50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
            115                 120                 125

Asp Glu Thr Ala Thr Ile Val Glu Phe Leu Asn Arg Trp Ile Thr Phe
        130                 135                 140

Cys Gln Ser Ile Ile Ser Thr Leu Thr Thr Thr Pro Ala Pro Arg
145                 150                 155                 160

Pro Pro Thr Pro Ala Pro Thr Ile Ala Ser Gln Pro Leu Ser Leu Arg
                165                 170                 175
```

```
Pro Glu Ala Cys Arg Pro Ala Ala Gly Gly Ala Val His Thr Arg Gly
            180                 185                 190

Leu Asp Phe Ala Cys Asp Ile Tyr Ile Trp Ala Pro Leu Ala Gly Thr
            195                 200                 205

Cys Gly Val Leu Leu Leu Ser Leu Val Ile Thr Leu Tyr Cys Arg Ser
            210                 215                 220

Lys Arg Ser Arg Leu Leu His Ser Asp Tyr Met Asn Met Thr Pro Arg
225                     230                 235                 240

Arg Pro Gly Pro Thr Arg Lys His Tyr Gln Pro Tyr Ala Pro Pro Arg
                245                 250                 255

Asp Phe Ala Ala Tyr Arg Ser Lys Arg Gly Arg Lys Lys Leu Leu Tyr
            260                 265                 270

Ile Phe Lys Gln Pro Phe Met Arg Pro Val Gln Thr Thr Gln Glu Glu
            275                 280                 285

Asp Gly Cys Ser Cys Arg Phe Pro Glu Glu Glu Glu Gly Gly Cys Glu
            290                 295                 300

Leu Arg Val Lys Phe Ser Arg Ser Ala Asp Ala Pro Ala Tyr Lys Gln
305                     310                 315                 320

Gly Gln Asn Gln Leu Tyr Asn Glu Leu Asn Leu Gly Arg Arg Glu Glu
                325                 330                 335

Tyr Asp Val Leu Asp Lys Arg Arg Gly Arg Asp Pro Glu Met Gly Gly
                340                 345                 350

Lys Pro Arg Arg Lys Asn Pro Gln Glu Gly Leu Tyr Asn Glu Leu Gln
                355                 360                 365

Lys Asp Lys Met Ala Glu Ala Tyr Ser Glu Ile Gly Met Lys Gly Glu
            370                 375                 380

Arg Arg Arg Gly Lys Gly His Asp Gly Leu Tyr Gln Gly Leu Ser Thr
385                     390                 395                 400

Ala Thr Lys Asp Thr Tyr Asp Ala Leu His Met Gln Ala Leu Pro Pro
                405                 410                 415

Arg
```

```
<210> SEQ ID NO 23
<211> LENGTH: 1251
<212> TYPE: DNA
<213> ORGANISM: Artificial Sequence
<220> FEATURE:
<223> OTHER INFORMATION: CD25-CAR 4
<220> FEATURE:
<221> NAME/KEY: misc_feature
<222> LOCATION: (1)..(459)
<223> OTHER INFORMATION: IL-2 receptor ligand
<220> FEATURE:
<221> NAME/KEY: misc_feature
<222> LOCATION: (460)..(594)
<223> OTHER INFORMATION: CD8H
<220> FEATURE:
<221> NAME/KEY: misc_feature
<222> LOCATION: (595)..(666)
<223> OTHER INFORMATION: CD8aTMD
<220> FEATURE:
<221> NAME/KEY: misc_feature
<222> LOCATION: (667)..(789)
<223> OTHER INFORMATION: CD28CD
<220> FEATURE:
<221> NAME/KEY: misc_feature
<222> LOCATION: (790)..(915)
<223> OTHER INFORMATION: 4-1BB/CD137CD
<220> FEATURE:
<221> NAME/KEY: misc_feature
<222> LOCATION: (916)..(1251)
<223> OTHER INFORMATION: CD3zeta
```

```
<400> SEQUENCE: 23
atgtaccgga tgcagctgct gagctgtatc gccctgtctc tggccctggt cacaaatagc      60
gcccctacca gcagcagcac caagaaaaca cagctgcaac tggaacacct cctgctggac     120
ctgcagatga tcctgaacgg catcaacaac tacaagaacc ccaagctgac ccggatgctg     180
accttcaagt tctacatgcc caagaaggcc accgagctga agcacctcca gtgcctggaa     240
gaggaactga agcccctgga agaagtgctg aatctggccc agagcaagaa cttccacctg     300
aggcctaggg acctgatcag caacatcaac gtgatcgtgc tggaactgaa aggcagcgag     360
acaaccttca tgtgcgagta cgccgacgag acagctacca tcgtggaatt tctgaaccgg     420
tggatcacct tctgccagag catcatcagc accctgacca ccacgacgcc agcgccgcga     480
ccaccaacac cggcgcccac catccgcgtcg cagcccctgt ccctgcgccc agaagcgtgc     540
cggccagcgg cggggggcgc agtgcacacg aggggggctgg acttcgcctg tgatatctac     600
atttgggccc ctctggctgg tacttgcggg gtcctgctgc tttcactcgt gatcactctt     660
tactgtagga gcaagcggag cagactgctg cacagcgact acatgaacat gacccccggg     720
aggcctggcc ccacccggaa gcactaccag ccctacgccc ctcccaggga tttcgccgcc     780
taccggagca aacggggcag aaagaaactc ctgtatatat tcaaacaacc atttatgaga     840
ccagtacaaa ctactcaaga ggaagatggc tgtagctgcc gatttccaga agaagaagaa     900
ggaggatgtg aactgagagt gaagttcagc aggagcgcag acgcccccgc gtacaagcag     960
ggccagaacc agctctataa cgagctcaat ctaggacgaa gagaggagta cgatgttttg    1020
gacaagagac gtggccggga ccctgagatg ggggggaaagc cgagaaggaa gaaccctcag    1080
gaaggcctgt acaatgaact gcagaaagat aagatggcgg aggcctacag tgagattggg    1140
atgaaaggcg agcgccggag gggcaagggg cacgatggcc tttaccaggg tctcagtaca    1200
gccaccaagg acacctacga cgcccttcac atgcaggccc tgcccctcg c              1251

<210> SEQ ID NO 24
<211> LENGTH: 1266
<212> TYPE: DNA
<213> ORGANISM: Artificial Sequence
<220> FEATURE:
<223> OTHER INFORMATION: CD25-CAR4 expression cassette
<220> FEATURE:
<221> NAME/KEY: misc_feature
<222> LOCATION: (13)..(471)
<223> OTHER INFORMATION: IL-2 receptor ligand
<220> FEATURE:
<221> NAME/KEY: misc_feature
<222> LOCATION: (472)..(606)
<223> OTHER INFORMATION: CD8H
<220> FEATURE:
<221> NAME/KEY: misc_feature
<222> LOCATION: (607)..(678)
<223> OTHER INFORMATION: CD8aTMD
<220> FEATURE:
<221> NAME/KEY: misc_feature
<222> LOCATION: (679)..(801)
<223> OTHER INFORMATION: CD28CD
<220> FEATURE:
<221> NAME/KEY: misc_feature
<222> LOCATION: (802)..(926)
<223> OTHER INFORMATION: 4-1BB/CD137CD
<220> FEATURE:
<221> NAME/KEY: misc_feature
<222> LOCATION: (927)..(1263)
<223> OTHER INFORMATION: CD3zeta

<400> SEQUENCE: 24
```

```
ctcgaggcca ccatgtaccg gatgcagctg ctgagctgta tcgccctgtc tctggccctg        60
gtcacaaata gcgcccctac cagcagcagc accaagaaaa cacagctgca actggaacac       120
ctcctgctgg acctgcagat gatcctgaac ggcatcaaca actacaagaa ccccaagctg       180
acccggatgc tgaccttcaa gttctacatg cccaagaagg ccaccgagct gaagcacctc       240
cagtgcctgg aagaggaact gaagcccctg gaagaagtgc tgaatctggc ccagagcaag       300
aacttccacc tgaggcctag ggacctgatc agcaacatca cgtgatcgt gctggaactg        360 aaaggcagcg agacaacctt catgtgcgag tacgccgacg agacagctac catcgtggaa       420
tttctgaacc ggtggatcac cttctgccag agcatcatca gcaccctgac caccacgacg       480
ccagcgccgc gaccaccaac accggcgccc accatcgcgt cgcagcccct gtccctgcgc       540
ccagaagcgt gccggccagc ggcggggggc gcagtgcaca cgaggggct ggacttcgcc        600 tgtgatatct acatttgggc ccctctggct ggtacttgcg gggtcctgct gctttcactc       660
gtgatcactc tttactgtag gagcaagcgg agcagactgc tgcacagcga ctacatgaac       720 atgaccccc ggaggcctgg ccccacccgg aagcactacc agccctacgc ccctcccagg        780
gatttcgccg cctaccggag caaacggggc agaaagaaac tcctgtatat attcaaacaa       840
ccatttatga ccagtaca aactactcaa gaggaagatg gctgtagctg ccgatttcca         900
gaagaagaag aaggaggatg tgaactgaga gtgaagttca gcaggagcgc agacgcccc        960 gcgtacaagc agggccagaa ccagctctat aacgagctca tctaggacg aagagaggag       1020 tacgatgttt tggacaagag acgtggccgg gaccctgaga tggggggaaa gccgagaagg      1080
aagaaccctc aggaaggcct gtacaatgaa ctgcagaaaa taagatggc ggaggcctac       1140 agtgagattg ggatgaaagg cgagcgccgg aggggcaagg ggcacgatgg cctttaccag      1200
ggtctcagta cagccaccaa ggacacctac gacgcccttc acatgcaggc cctgcccccct     1260 cgctaa                                                                 1266
```

```
<210> SEQ ID NO 25
<211> LENGTH: 2604
<212> TYPE: DNA
<213> ORGANISM: Artificial Sequence
<220> FEATURE:
<223> OTHER INFORMATION: CD25-CAR4 expression cassette with EF1alpha
      promoter
<220> FEATURE:
<221> NAME/KEY: misc_feature
<222> LOCATION: (1)..(1335)
<223> OTHER INFORMATION: EF1alpha promoter
<220> FEATURE:
<221> NAME/KEY: misc_feature
<222> LOCATION: (1351)..(1809)
<223> OTHER INFORMATION: IL-2 receptor ligand
<220> FEATURE:
<221> NAME/KEY: misc_feature
<222> LOCATION: (1810)..(1944)
<223> OTHER INFORMATION: CD8H
<220> FEATURE:
<221> NAME/KEY: misc_feature
<222> LOCATION: (1945)..(2016)
<223> OTHER INFORMATION: CD8aTMD
<220> FEATURE:
<221> NAME/KEY: misc_feature
<222> LOCATION: (2017)..(2139)
<223> OTHER INFORMATION: CD28CD
<220> FEATURE:
<221> NAME/KEY: misc_feature
<222> LOCATION: (2140)..(2264)
<223> OTHER INFORMATION: 4-1BB/CD137CD
<220> FEATURE:
<221> NAME/KEY: misc_feature
<222> LOCATION: (2265)..(2601)
```

<223> OTHER INFORMATION: CD3zeta

<400> SEQUENCE: 25

```
gagtaattca tacaaaagga ctcgccctg ccttggggaa tcccagggac cgtcgttaaa    60
ctcccactaa cgtagaaccc agagatcgct gcgttcccgc cccctcaccc gcccgctctc   120
gtcatcactg aggtggagaa gagcatgcgt gaggctccgg tgcccgtcag tgggcagagc   180
gcacatcgcc cacagtcccc gagaagttgg ggggaggggt cggcaattga accggtgcct   240
agagaaggtg gcgcggggta aactgggaaa gtgatgtcgt gtactggctc cgccttttc   300 ccgaggtgg gggagaaccg tatataagtg cagtagtcgc cgtgaacgtt cttttcgca   360 acgggtttgc cgccagaaca caggtaagtg ccgtgtgtgg ttcccgcggg cctggcctct   420
ttacgggtta tggcccttgc gtgccttgaa ttacttccac gccctggct gcagtacgtg   480 attcttgatc ccgagcttcg ggttggaagt gggtgggaga gttcgaggcc ttgcgcttaa   540
ggagcccctt cgcctcgtgc ttgagttgag gcctggcttg ggcgctgggg ccgccgcgtg   600
cgaatctggt ggcaccttcg cgcctgtctc gctgctttcg ataagtctct agccatttaa   660
aatttttgat gacctgctgc gacgctttt ttctggcaag atagtcttgt aaatgcgggc   720
caagatctgc acactggtat ttcggttttt ggggccgcgg gcggcgacgg ggcccgtgcg   780
tcccagcgca catgttcggc gaggcggggc ctgcgagcgc ggccaccgag aatcggacgg   840
gggtagtctc aagctggccg gcctgctctg gtgcctggcc tcgcgccgcc gtgtatcgcc   900
ccgccctggg cggcaaggct ggcccggtcg gcaccagttg cgtgagcgga aagatggccg  960
cttcccggcc ctgctgcagg gagctcaaaa tggaggacgc ggcgctcggg agagcgggcg  1020
ggtgagtcac ccacacaaag gaaaagggcc tttccgtcct cagccgtcgc ttcatgtgac  1080
tccacggagt accgggcgcc gtccaggcac ctcgattagt tctcgagctt ttggagtacg  1140
tcgtctttag gttgggggga ggggtttat gcgatggagt ttccccacac tgagtgggtg  1200
gagactgaag ttaggccagc ttggcacttg atgtaattct ccttggaatt tgcccttttt  1260
gagtttggat cttggttcat tctcaagcct cagacagtgg ttcaaagttt ttttcttcca  1320
tttcaggtgt cgtgattcga attcgccacc atgtaccgga tgcagctgct gagctgtatc  1380
gccctgtctc tggccctggt cacaaatagc gcccctacca gcagcagcac caagaaaaca  1440
cagctgcaac tggaacacct cctgctggac ctgcagatga tcctgaacgg catcaacaac  1500
tacaagaacc ccaagctgac ccggatgctg accttcaagt ctacatgcc caagaaggcc  1560 accgagctga gcacctcca gtgcctggaa gaggaactga gcccctgga agaagtgctg  1620 aatctggccc agagcaagaa cttccacctg aggcctaggg acctgatcag caacatcaac  1680
gtgatcgtgc tggaactgaa aggcagcgag acaaccttca tgtgcgagta cgccgacgag  1740
acagctacca tcgtggaatt tctgaaccgg tggatcacct tctgccagag catcatcagc  1800
accctgacca ccacgacgcc agcgccgcga ccaccaacac cggcgcccac catcgcgtcg  1860 cagccctgt ccctgcgccc agaagcgtgc cggccagcgg cgggggcgc agtgcacacg  1920 aggggggctgg acttcgcctg tgatatctac atttgggccc ctctggctgg tacttgcggg  1980
gtcctgctgc tttcactcgt gatcactctt tactgtagga gcaagcggag cagactgctg  2040
cacagcgact acatgaacat gacccccgg aggcctggcc ccaccggaa gcactaccag  2100 ccctacgccc ctcccaggga tttgccgcc taccggagca aacggggcag aaagaaactc  2160
ctgtatatat tcaaacaacc atttatgaga ccagtacaaa ctactcaaga ggaagatggc  2220
tgtagctgcc gatttccaga agaagaagaa ggaggatgtg aactgagagt gaagttcagc  2280
```

-continued

```
aggagcgcag acgcccccgc gtacaagcag ggccagaacc agctctataa cgagctcaat   2340
ctaggacgaa gagaggagta cgatgttttg gacaagagac gtggccggga ccctgagatg   2400
gggggaaagc cgagaaggaa gaaccctcag gaaggcctgt acaatgaact gcagaaagat   2460
aagatggcgg aggcctacag tgagattggg atgaaaggcg agcgccggag gggcaagggg   2520
cacgatggcc tttaccaggg tctcagtaca gccaccaagg acacctacga cgcccttcac   2580
atgcaggccc tgccccctcg ctaa                                          2604
```

CD25 CHIMERIC ANTIGEN RECEPTORS AND USES THEREOF

PRIORITY CLAIM

This application is a 371 National Phase Application of PCT Application No. PCT/US2020/048574 entitled "CD25 CHIMERIC ANTIGEN RECEPTORS AND USES THEREOF" filed on Aug. 28, 2020, which claims the benefit of U.S. Provisional Patent Appl. No. 62/893,039, filed on Aug. 28, 2019, the contents of which are hereby incorporated by reference in their entirety into the present application.

SEQUENCE LISTING

This application contains a Sequence Listing, which was submitted in ASCII format via EFS-Web, and is hereby incorporated by reference in its entirety. The ASCII copy, created on Feb. 24, 2022, is name Sequence Listing and is 25 KB in size.

BACKGROUND

Adult T cell leukemia/lymphoma (ATLL) is a rare and often aggressive form of T cell lymphoma, classified into several forms: acute, chronic, smouldering, and lymphoma. The prognosis of ATLL is poor, with a median survival of less than one year and projected 4-year survival of only about 5% for the most common acute and lymphoma forms; while the chronic and smouldering forms have a projected 4-year survival of 26.9% and 62%, respectively. Treatment options for ATLL is limited because patients usually have a poor response to chemotherapy regimens that are normally effective in aggressive lymphomas, and alternative therapies have had limited efficacy. Consequently, targeted and effective therapies to target ATLL and other T cell malignancies are needed.

While the immunophenotype of ATLL cells is similar to activated mature T-lymphocytes, the most characteristic feature of ATLL cells is strong expression of the alpha chain of the interleukin-2 (IL-2) receptor (IL-2R, which is also known as CD25 (Matutes 2007). Such expression may also be seen in other T-cell malignancies, making CD25 a viable target for developing drugs against ATLL and other conditions. For example, fusion toxins such as denileukin diftitox (Ontak®) have previously been used to treat CD25+ lymphomas, but their clinical effectiveness has been limited due to serious side effects from vascular leak toxicity and production issues related to purity and aggregation, leading to Ontak being discontinued. (Williams et al. 1990; Dang et al. 2004; see also www.accessdata.fda.gov/scripts/drugshortages/dsp_ActiveIngredientDetails.cfm?AI=De nileukin+Diftitox+%280ntak%29+ Injection&st=d&tab=tabs-2). Thus, there is a need for developing new or alternative therapies against ATLL and other conditions.

SUMMARY

According to the embodiments described herein, a chimeric antigen receptor (CAR) that targets CD25 is provided. In some aspects, the CAR includes a CD25 targeting component and a non-specific CAR complex. The non-specific CAR complex may include a hinge region, a transmembrane region, and an intracellular signaling domain according to some embodiments. In some embodiments, the non-specific CAR complex may also include one or more costimulatory domains.

In some embodiments, the CD25 targeting component is an IL-2 receptor ligand or a portion thereof. In one embodiment, the IL-2 receptor ligand comprises human IL-2 (SEQ ID NO:21) or a portion thereof.

In some embodiments, the non-specific CAR complex of the hinge region is an IgG based hinge region, a CD8 hinge region, or a CD28 hinge region. In certain embodiments, an IgG based hinge region may include SEQ ID NO:1, SEQ ID NO:2, or SEQ ID NO:3; a CD8 hinge region may include SEQ ID NO:4 or SEQ ID NO:5; and a CD28 hinge region may include SEQ ID NO:6.

In some embodiments, the transmembrane region is a CD3 transmembrane region of the non-specific CAR complex is a CD28 transmembrane region or a CD8 transmembrane region. In certain embodiments, a CD3 transmembrane region may include SEQ ID NO:7, SEQ ID NO:8, SEQ ID NO:9, or SEQ ID NO:10; a CD28 transmembrane region may include SEQ ID NO:11; or a CD8 transmembrane region may include SEQ ID NO:12 or SEQ ID NO:13.

In some embodiments, the intracellular signaling domain of the non-specific CAR complex is a CD3-zeta (CD3ζ) intracellular signaling domain. In one embodiment, the CD3ζ intracellular signaling domain may include SEQ ID NO:14 or a portion thereof.

In certain embodiments, the one or more costimulatory domains of the non-specific CAR complex is a CD28 costimulatory domain, an inducible costimulatory molecule (ICOS), a 4-1BB costimulatory domain, an OX40 costimulatory domain, or a CD27 stimulatory domain. In certain aspects, the non-specific CAR complex includes 1 or 2 of the aforementioned costimulatory domains. In some embodiments, the CD28 costimulatory domain may include SEQ ID NO:15 or a portion thereof; the inducible costimulatory molecule (ICOS) may include SEQ ID NO:16 or a portion thereof; the 4-1BB costimulatory domain may include SEQ ID NO:17 or a portion thereof; the OX40 costimulatory domain may include SEQ ID NO:18 or a portion thereof; or the CD27 stimulatory domain may include SEQ ID NO:19 or a portion thereof.

In one embodiment, the CAR that targets CD25 has an amino acid sequence that includes SEQ ID NO:22.

A nucleotide sequence encoding the CARs described above is also provided in some embodiments. In certain embodiments, the nucleotide sequence includes SEQ ID NO:23.

An expression cassette that includes a nucleotide sequence encoding the CARs described above is also provided according to some embodiments. In certain embodiments, the expression cassette includes a nucleotide sequence comprising SEQ ID NO:23, SEQ ID NO:24, or SEQ ID NO:25.

A retroviral vector that includes an expression cassette comprising a nucleotide sequence encoding the CARs described above is also provided according to some embodiments.

A T cell or population of T cells that express a CAR that targets CD25 as described above is also provided in accordance with some embodiments. Such cells may be used to treat a disease or condition associated with expression of CD25. Thus, a method of treating a subject having a disease or condition is provided in accordance with some embodiments. In certain embodiments, the method includes a step of administering a population of T cells that express a CAR that targets CD25 to the subject as described according to some embodiments. According to some embodiments, the population of T cells administered to the subject may be autologous or allogenic to the subject.

In some embodiments, the disease or condition treated using the T cell population described above is a T cell malignancy or a lymphoma selected from Adult T-cell Leukemia Lymphoma, Peripheral T-cell Lymphoma, Cutaneous T-cell Lymphoma, Diffuse large B-cell Lymphoma, Follicular Lymphoma, Burkitt's Lymphoma, Anaplastic large cell Lymphoma, or Angioimmunoblastic T-cell Lymphoma. In other embodiments, the disease or condition is an autoimmune or transplant-associated condition selected from graft-versus-host-disease, scleroderma, psoriasis, rheumatoid arthritis, or systemic lupus erythematosus.

A T cell or population of T cells that express a CAR that targets CD25 as described above is also provided in accordance with some embodiments. Such cells may be used to activate the immune system in a subject. Accordingly, a method of activating the immune system in a subject is provided in accordance with some embodiments. In certain embodiments, the method includes a step of administering a population of T cells that express a CAR that targets CD25 to the subject as described according to some embodiments. According to some embodiments, the population of T cells administered to the subject may be autologous or allogenic to the subject. According to some embodiments, the population of T cells are administered by intravenous infusion. In certain embodiments, administering the population of T cells increases the release of a cytokine from a target cell. For example, in certain embodiments the target cell exhibits an increased release of the cytokine Interleukin-2 (IL-2) or Interferon gamma (IFNγ).

A T cell or population of T cells that express a CAR that targets CD25 as described above is also provided in accordance with some embodiments. Such cells may be used kill a target cell or a population of target cells in a subject. Accordingly, a killing a target cell is provided in accordance with some embodiments. In certain embodiments, the method includes a step of administering a population of T cells that express a CAR that targets CD25 to the subject as described according to some embodiments. According to some embodiments, the population of T cells administered to the subject may be autologous or allogenic to the subject. According to some embodiments, the population of T cells are administered by intravenous infusion. In certain embodiments, administering the population of T cells is cytotoxic to the target cell.

BRIEF DESCRIPTION OF THE DRAWINGS

FIG. 2 is a certificate of analysis for the pMSGV-IL-2-ligand-h(28BBζ)-3rd-CAR construct, including a quality control (QC) analysis and a restriction digestion map confirming expected fragment sizes of the construct.

FIG. 3 is a sequence alignment resulting from Sanger sequencing confirming that the sequence of the constructed plasmid pMSGV-IL-2-ligand-h(28BBζ)-3rd-CAR was in accordance with the design.

FIG. 5 is a certificate of analysis for the pCDH-EF1a-IL-2-ligand-h(28BBζ)-3rd-CAR construct, including a quality control (QC) analysis and a restriction digestion map confirming expected fragment sizes of the construct.

FIG. 6 is a sequence alignment resulting from Sanger sequencing confirming that the sequence of the constructed plasmid pCDH-EF1a-IL-2-ligand-h(28BBζ)-3rd-CAR was in accordance with the design.

FIG. 7 shows Albumin (ALB) (left panel) and Woodchuck Hepatitis Virus (WHP) Posttranscriptional Regulatory Element (WPRE) (right panel) qPCR standard curves used to calculate lentivirus titer.

FIG. 8 shows pCDH-EF1a-IL-2-ligand-h(28BBζ)-3rd-CAR expression in Jurkat cells.

FIG. 11 shows two fluorescence-activated cell sorting (FACS) plots showing positive CAR-T cells for primary T cells transfected with a control lentiviral vector (Con-T+PE-anti-IL-2, left) and a lentiviral vector expressing the pMSGV-IL-2-ligand-h(28BBζ)-3rd-CAR construct (W122618-1BCAR-T+PE-anti-IL-2, right).

FIG. 12 shows two bar graphs quantifying cytotoxicity in co-culture experiments using target cells having CD25 (left, Target Cell:CHO-CD25-Luciferase) and control CHO cells without CD25 (right, Target Cell:CHO-S-Luciferase). Cells were co-transfected with control T cells (Con-T) or T cells expressing the pMSGV-IL-2-ligand-h(28BBζ)-3rd-CAR construct (W122618-1BCAR-T).

FIG. 13 shows experimental results quantifying cytokine release in experimental and control (Con-T) cells. Two standard curves for cytokines IL-2 (upper left) and Interferon gamma (IFNγ, upper right) are shown measuring optical density (O.D.) versus protein concentration. Two bar graphs show quantification of IL-2 (lower left) and IFNγ (lower right) in target cells when co-transfected with control T cells (Con-T) or T cells expressing the pMSGV-IL-2-ligand-h(28BBζ)-3rd-CAR construct (W122618-1BCAR-T).

FIG. 14 depicts a graph quantifying cell proliferation in cells following lentiviral transfection with either the control lentiviral vector (Con-T) or the experimental lentiviral vector expressing the pMSGV-IL-2-ligand-h(28BBζ)-3rd-CAR construct (W122618-1B CAR-T). Quantification of T cell proliferation (as measured by number of viable cells) is displayed in a table below on Days 1 to 8 (D1-D8) (n.s.).

DETAILED DESCRIPTION

Figure 1:
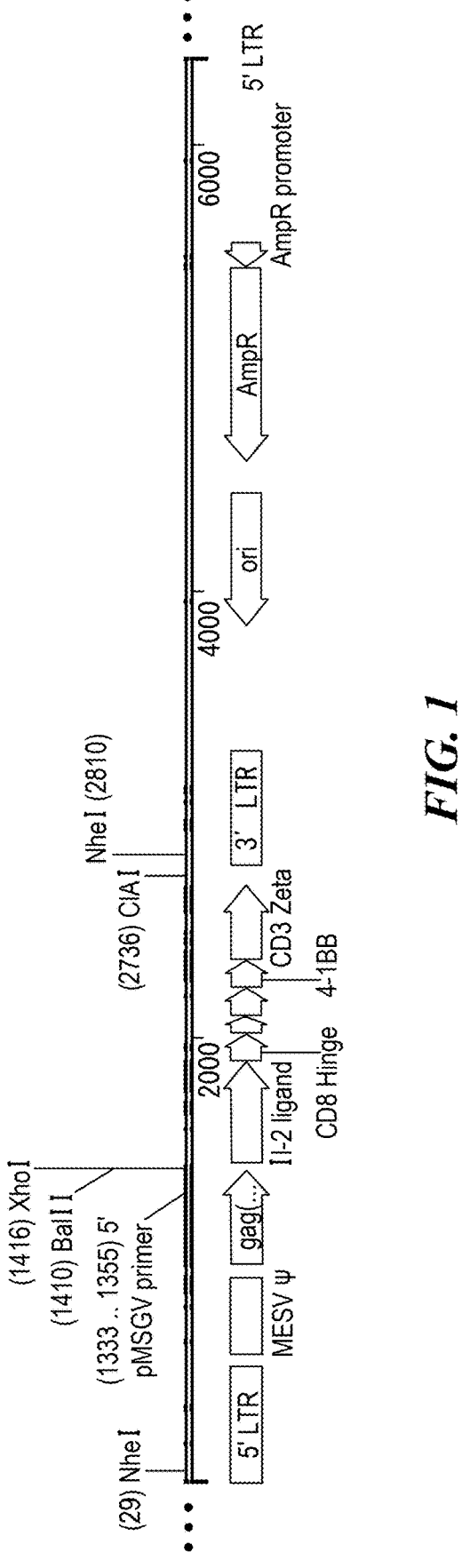
FIG. 1 is a schematic of the construction of an MSGV retroviral vector having a CD25-CAR gene insert (pMSGV-IL-2-ligand-h(28BBζ)-3rd-CAR).

Chimeric antigen receptors (CAR) that target the alpha chain of the interleukin-2 (IL-2) receptor (also known as CD25) (CD25-CAR), nucleotides that encode CD25-CARs, T cells expressing CD25 CAR, and methods for treating conditions using the same are provided herein.

Chimeric antigen receptors are artificially engineered fusion proteins that form receptors having specificity to a target cell, for example, cancer cells or immune cells. Grafting the specificity of a monoclonal antibody onto a T cell gives a CAR-T. The basic principle of CAR-T cell design involves recombinant receptors that combine antigen-binding and T-cell activating functions. The general premise of CAR-T cells is to artificially generate T-cells targeted to markers found on cancer cells. CAR-Ts can be derived from either a patient's own blood (autologous) or derived from another healthy donor (allogenic). The expressed artificial T cell receptor is MHC independent and thus the targeting efficiency is greatly increased. During therapy, the CAR-T cells destroy cancer cells through mechanisms such as extensive stimulated cell proliferation, increasing the degree to which the cell is toxic to other living cells i.e. cytotoxicity, and by causing the increased production of factors that are secreted from cells in the immune system that have an effect on other cells in the organism.

According to some embodiments the CD25-CARs described herein include a non-specific CAR complex (ns-CAR complex) and a CD25 targeting component.

The non-specific CAR complex of the CD25-CAR is designed to include one or more of the following components: a hinge region, a transmembrane region, a costimulatory domain, and an intracellular signaling domain. The components of the non-specific CAR complex form a fusion protein that is fused to the CD25 targeting component.

According to the embodiments described herein, the hinge region separates the CD25 targeting component from the transmembrane region of the non-specific CAR complex and is based on immunoglobulin (Ig)-like domain hinges. In some embodiments, the hinge region is an IgG based hinge region derived from an IgG1, IgG2, or IgG4, which may include all or a portion of the IgG hinge regions below:

```
IgG1 hinge:
EPKSCDKTHTCP
```

(SEQ ID NO: 1; full sequence information found at www.uniprot.org/uniprot/P01857)

```
IgG2 hinge:
ERKCCVECPPCP
```

(SEQ ID NO: 2; full sequence information found at www.uniprot.org/uniprot/P01859)

```
IgG4 hinge:
ESKYGPPCPSCP
```

(SEQ ID NO: 3; full sequence information found at www.uniprot.org/uniprot/P01861)

In certain embodiments, a hinge region derived from an IgG may also include a CH2 region of the IgG, a CH3 region of the IgG, both a CH2 and a CH3 region of the IgG, or the hinge region may be a short hinge lacking a CH2 or CH3 region (see full sequence information above). In certain aspects, the CH2 or CH3 region, when used as part of the hinge region, may be mutated to alter or improve CAR T cell functionality.

In other embodiments, the hinge region may be an Ig-based hinge from a native T cell molecule, in which case the hinge may include a CD28 hinge or a CD8 hinge. In some embodiments, the CD28 or CD8 hinge may include a portion (e.g., 40-50 amino acids) of the C terminal of the extracellular domains below:

```
CD8a extracellular domain:
SQFRVSPLDRTWNLGETVELKCQVLLSNPTSGCSWLFQPRGAAASPTFL

LYLSQNKPKAAEGLDTQRFSGKRLGDTFVLTLSDFRRENEGYYFCSALS

NSIMYFSHFVPVFLPAKPTTTPAPRPPTPAPTIASQPLSLRPEACRPAA

GGAVHTRGLDFACD
```

-continued (SEQ ID NO: 4; full sequence information found at www.uniprot.org/uniprot/P01732)

```
CD8b extracellular domain:
LQQTPAYIKVQTNKMVMLSCEAKISLSNMRIYWLRQRQAPSSDSHHEFL

ALWDSAKGTIHGEEVEQEKIAVFRDASRFILNLTSVKPEDSGIYFCMIV

GSPELTFGKGTQLSWDFLPTTAQPTKKSTLKKRVCRLPRPETQKGPLCS

P
```

(SEQ ID NO: 5; full sequence information found at www.uniprot.org/uniprot/P10966)

```
CD28 extracellular domain:
NKILVKQSPMLVAYDNAVNLSCKYSYNLFSREFRASLHKGLDSAVEVCV

VYGNYSQQLQVYSKTGFNCDGKLGNESVTFYLQNLYVNQTDIYFCKIEV

MYPPPYLDNEKSNGTIIHVKGKHLCPSPLFPGPSKP
```

(SEQ ID NO: 6; full sequence information found at www.uniprot.org/uniprot/P10747)

The transmembrane region of the non-specific CAR complex is a hydrophobic region of the CAR that spans the cell membrane. In certain embodiments, the transmembrane region includes a CD3 transmembrane domain or portion thereof, a CD28 transmembrane domain or portion thereof, or a CD8 transmembrane domain or portion thereof. In some embodiments, the transmembrane domain may include all or a portion of one of the transmembrane domains (TMDs) below:

```
CD3δ TMD:
GIIVTDVIATLLLALGVFCFA
```

(SEQ ID NO: 7; full sequence information found at www.uniprot.org/uniprot/P04234)

```
CD3ε TMD:
VMSVATIVIVDICITGGLLLLVYYWS
```

(SEQ ID NO: 8; full sequence information found at www.uniprot.org/uniprot/P07766)

```
CD3γ TMD:
GFLFAEIVSIFVLAVGVYFIA
```

(SEQ ID NO: 9; full sequence information found at www.uniprot.org/uniprot/P09693)

```
CDζ TMD:
LCYLLDGILFIYGVILTALFL
```

(SEQ ID NO: 10; full sequence information found at www.uniprot.org/uniprot/P20963)

```
CD28 TMD:
FWVLVVVGGVLACYSLLVTVAFIIFWV
```

(SEQ ID NO: 11; full sequence information found at www.uniprot.org/uniprot/P10747)

7

-continued

```
CD8a TMD:
IYIWAPLAGTCGVLLLSLVIT (SEQ ID NO: 12; full sequence information found at www.uniprot.org/uniprot/P01732)

CD8b TMD:
ITLGLLVAGVLVLLVSLGVAI (SEQ ID NO: 13; full sequence information found at www.uniprot.org/uniprot/P10966)
```

According to the embodiments described herein, the non-specific CAR complex includes an intracellular signaling domain that includes a cytoplasmic signaling domain of a T cell Receptor (TCR), e.g., an CD3-gamma intracellular signaling domain, a CD3-delta intracellular signaling domain, a CD3-epsilon intracellular signaling domain, or a CD3-zeta intracellular signaling domain (see sequence information above). In certain embodiments, the intracellular signaling domain includes a CD3-zeta (CD3ζ) intracellular signaling domain, which may include all or a portion of its cytoplasmic domain sequence RVKFSRSADAPA-YQQGQNQLYNELNLGRREEYDVLDKRRGRDP EMGGKPQRRKNPQEGLYNELQKDKMAEAYSEI-GMKGERRRGKGHDGLYQGLSTATK DTY-DALHMQALPPR (SEQ ID NO:14; full sequence information found at https://www.uniprot.org/uniprot/P20963).

In certain embodiments, the non-specific CAR complex also includes one or more costimulatory domains in addition to the intracellular signaling domain. Suitable costimulatory domains that may be used in accordance with the embodiments described herein may include, but are not limited to, a CD28 costimulatory domain, which may include all or a portion of its cytoplasmic domain sequence RSKRSRLLHSDYMNMTPRRPGPTRKHYQPYAPPRD-FAAYRS (SEQ ID NO:15; full sequence information found at https://www.uniprot.org/uniprot/P10747), an inducible costimulatory molecule (ICOS), which may include all or a portion of its cytoplasmic domain sequence CWLTKKKYSSSVHDPNGEYMFMRAVN-TAKKSRLTDVTL (SEQ ID NO:16; full sequence information found at www.uniprot.org/uniprot/Q9Y6W8), a 4-1BB costimulatory domain (also known as CD137), which may include all or a portion of its cytoplasmic domain sequence KRGRKKLLYIFKQPFMRPVQTTQEEDGCSCRFPEE EEGGCEL (SEQ ID NO:17; full sequence information found at www.uniprot.org/uniprot/Q07011), an OX40 costimulatory domain (also known as CD134) which may include all or a portion of its cytoplasmic domain sequence ALYLLRRDQRLPPDAHKPPGGGSFRTPIQEEQADAH-STLAKI (SEQ ID NO:18; full sequence information found at www.uniprot.org/uniprot/P43489), or a CD27 costimulatory domain which may include all or a portion of its cytoplasmic domain sequence QRRKYRSNKGESPVE-PAEPCHYSCPREEEGSTIPIQEDYRKPEPACSP (SEQ ID NO:19; full sequence information found at www.uniprot.org/uniprot/P26842). In some embodiments, the non-specific CAR complex includes no costimulatory domains, in other embodiments, the non-specific CAR complex includes one costimulatory domain, and in other embodiments, the non-specific CAR complex includes two costimulatory domains.

In certain embodiments, the non-specific CAR complex includes a hinge region selected from those described herein, a transmembrane region selected from those described herein, and a CD3ζ intracellular signaling domain to form a first generation nsCAR complex (nsCAR complex 1). In certain embodiments, the non-specific CAR complex includes a hinge region selected from those described herein, a transmembrane region selected from those described herein, one or more costimulatory signaling domains selected from those described herein, and a CD3ζ intracellular signaling domain to form a second (or third) generation nsCAR complex (nsCAR complex 2). In one embodiment, the non-specific CAR complex includes a hinge region selected from those described herein, a transmembrane region selected from those described herein, two costimulatory signaling domains selected from those described herein, and a CD3ζ intracellular signaling domain to form a third generation nsCAR complex (nsCAR complex 3). In the embodiments described above, the components of the non-specific CAR complex are fused to each other and arranged as follows to form nsCAR complexes (H=hinge; TM=transmembrane domain; CD=costimulatory domain; $n \geq 1$):

| | |
|---|---|
| 5'-(H)-(TM)-(CD3ζ)-3' | (nsCAR complex 1) |
| 5'-(H)-(TM)-(CD)$_n$-(CD3ζ)-3' | (nsCAR complex 2) |
| 5'-(H)-(TM)-(CD)-(CD)-(CD3ζ)-3' | (nsCAR complex 3) |

In some embodiments, the non-specific CAR complexes described above include a hinge region and a transmembrane region derived from the same molecule. In those embodiments, the hinge and transmembrane regions are effectively a single domain that includes two adjacent regions of the same molecule but may be referred to as separate regions for purposes of describing the non-specific CAR complex.

In certain embodiments, the non-specific CAR complex includes a hinge region of a CD8 molecule (CD8$_H$), a transmembrane region of a CD8 molecule (CD8$_{TM}$), a CD28 costimulatory domain that includes a cytoplasmic portion of CD28 (CD28$_{CD}$), a 4-1BB costimulatory domain (4-1BB$_{CD}$) that includes a cytoplasmic portion of a 4-1BB, and a CD3ζ intracellular signaling domain. In some embodiments, the nsCAR complex includes components arranged in the following order to form nsCAR complex 4:

5'-(CD8$_H$)-(CD8$_{TM}$)-(CD28$_{CD}$)-(4-1BB$_{CD}$)-(CD3ζ)-3' (nsCAR complex 4)

In one embodiment, the amino acid sequence of the non-specific CAR complex components includes the following sequences:

```
CD8_H and CD8_TM (combined, CD8_H portion underlined)
                                       (SEQ ID NO: 20)
TTTPAPRPPTPAPTIASQPLSLRPEACRPAAGGAVHTRGLDFACDIYIWA

PLAGTCGVLLLSLVITLYC

CD28_CD
                                       (SEQ ID NO: 15)
RSKRSRLLHSDYMNMTPRRPGPTRKHYQPYAPPRDFAAYRS 4-1BB_CD
                                       (SEQ ID NO: 17)
KRGRKKLLYIFKQPFMRPVQTTQEEDGCSCRFPEEEEGGCEL

CD3ζ
                                       (SEQ ID NO: 14)
RVKFSRSADAPAYKQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR-
```

The CD25 targeting component may be any suitable protein or peptide able to bind CD25 and activate signaling by the components of the non-specific CAR complex. In certain embodiments, the CD25 targeting component is an interleukin-2 receptor ligand. In other embodiments, the CD25 targeting component may be an immune-binding portion of an anti-CD25 antibody (e.g., Fab, scFv, single domain antibody or nanobody, etc.). In some embodiments, the CD25 targeting component is an IL-2 receptor ligand. The IL-2 receptor ligand may be derived from a native IL-2 receptor ligand, or it may be a recombinant or synthetic IL-2 receptor ligand. In one embodiment, the IL-2 receptor ligand is human IL-2 (hIL-2), which may include all or a portion of: MYRMQLLSCIALSLALVTN-SAPTSSSTKKTQLQLEHLLLDLQMILNGINNYK NPKLTRMLTFKFYMPK-KATELKHLQCLEEELKPLEEVLNLAQSKNFHLR-PRDLISNINVI VLELKGSETTFMCEYADETATIVE-FLNRWITFCQSIISTLT (SEQ ID NO:21; full sequence information found at www.uniprot.org/uniprot/P60568)

According to the embodiments described herein, the CD25 targeting component and the non-specific CAR complex together form a CD25-CAR. In certain embodiments, the CD25-CAR includes a CD25 targeting component selected from those described herein, a hinge region selected from those described herein, a transmembrane region selected from those described herein, and a CD3ζ intracellular signaling domain to form a first generation nsCAR complex (CD25-CAR 1). In certain embodiments, the CD25-CAR includes a CD25 targeting component selected from those described herein, a hinge region selected from those described herein, a transmembrane region selected from those described herein, one or more costimulatory signaling domains selected from those described herein, and a CD3ζ intracellular signaling domain to form a second (or third) generation nsCAR complex (CD25-CAR 2). In one embodiment, the CD25-CAR includes a CD25 targeting component selected from those described herein, a hinge region selected from those described herein, a transmembrane region selected from those described herein, two costimulatory signaling domains selected from those described herein, and a CD3ζ intracellular signaling domain to form a third generation nsCAR complex (CD25-CAR 3). In the embodiments described above, the components of the CD25 targeting component and the non-specific CAR complex are fused to each other and arranged as follows to form CD25-CARs (CD25$_{TC}$=CD25 targeting component; H=hinge; TM=transmembrane domain; CD=costimulatory domain; n≥1):

5'-(CD25$_{TC}$)-(H)-(TM)-(CD3ζ)-3'        (CD25-CAR 1)

5'-(CD25$_{TC}$)-(H)-(TM)-(CD)$_n$-(CD3ζ)-3'        (CD25-CAR 2)

5'-(CD25$_{TC}$)-(H)-(TM)-(CD)-(CD)-(CD3ζ)-3'        (CD25-CAR 3)

In one embodiment, the CD25-CAR includes hIL-2 fused to nsCAR complex 4 to form CD25-CAR4, the components of which are fused to each other and arranged as follows:

5'-(hIL-2)-(CD8$_H$)-(CD8$_{TM}$)-(CD28$_{CD}$)-(4-1BB$_{CD}$)-
(CD3ζ)-3'        (CD25-CAR 4)

In one embodiment, the amino acid sequence of CD25-CAR4 is shown below (hIL-2=normal text; CD8$_H$ and CD8$_{TM}$=underlined; CD28$_{CD}$=bold; 4-1BB$_{CD}$=italics; CD3ζ=italics+underlined):

(CD25-CAR 4 SEQ ID NO: 22)
MYRMQLLSCIALSLALVTNSAPTSSSTKKTQLQLEHLLLDLQMILNGINN

YKNPKLTRMLTFKFYMPKKATELKHLQCLEEELKPLEEVLNLAQSKNFHL

RPRDLISNINVIVLELKGSETTFMCEYADETATIVEFLNRWITFCQSIIS

TLTTTTPAPRPPTPAPTIASQPLSLRPEACRPAAGGAVHTRGLDFACDIY

IWAPLAGTCGVLLLSLVITLYCRSKRSRLLHSDYMNMTPRRPGPTRKHYQ

PYAPPRDFAAYRS_KRGRKKLLYIFKQPFMRPVQTTQEEDGCSCRFPEEEE_

_GGCRLRVKFSRSADAPAYKQGQNQLYNELNLGRREEYDVLDKRRGRDPEM_

_GGKPRRKNPQEGLYNELQKDKMAEAYSEIGMKGERRRGKGHDGLYQGLST_

_ATKDTYDALHMQALPPR-_

In certain embodiments, a nucleic acid molecule that encodes a CD25-CAR (CD25-CAR gene) is provided. Nucleic acid molecules (i.e., CD25-CAR genes) that encode a desired CD25-CAR may include a nucleotide sequence corresponding to any sequence of degenerate codons that give rise to the desired CD25-CAR amino acid sequence in accordance with the genetic code. In certain embodiments, a CD25-CAR 1 gene, a CD25-CAR 2 gene, or a CD25-CAR 3 gene has a nucleotide sequence that corresponds to a sequence of degenerate codons giving rise to a CD25-CAR 1, a CD25-CAR 2, or a CD25-CAR 3 (described above), respectively.

In some embodiments, the CD25-CAR gene includes a nucleic acid sequence that corresponds to a sequence of degenerate codons giving rise to CD25-CAR 4, which includes the following components as described above arranged in the following order to form nsCAR complex 4:

5'-(hIL-2)-(CD8$_H$)-(CD8$_{TM}$)-(CD28$_{CD}$)-(4-1BB$_{CD}$)-
(CD3ζ)-3'        (CD25-CAR 4)

In one embodiment, the nucleic acid sequence of CD25-CAR4 is shown below (hIL-2=normal text; CD8$_H$ and CD8$_{TM}$=underlined; CD28$_{CD}$=bold; 4-1BB$_{CD}$=italics; CD3ζ=italics+underlined):

(SEQ ID NO: 23)
atgtaccggatgcagctgctgagctgtatcgccctgtctctggccctggt cacaaatagcgcccctaccagcagcagcaccaagaaaacacagctgcaac tggaacacctcctgctggacctgcagatgatcctgaacggcatcaacaac tacaagaaccccaagctgacccggatgctgaccttcaagttctacatgcc caagaaggccaccgagctgaagcacctccagtgcctggaagaggaactga agcccctggaagaagtgctgaatctggcccagagcaagaacttccacctg aggcctagggacctgatcagcaacatcaacgtgatcgtgctggaactgaa aggcagcgagacaaccttcatgtgcgagtacgccgacgagacagctacca tcgtggaatttctgaaccggtggatcaccttctgccagagcatcatcagc accctgacc_accacgacgccagcgccgcgaccaccaacaccggcgcccac_

_catcgcgtcgcagcccctgtccctgcgcccagaagcgtgccggccagcgg_

_cgggggggcgcagtgcacacgagggggctggacttcgcctgtgatatctac_

_atttgggccctctggctggtacttgcggggtcctgctgctttcactcgt_

_gatcactctttactgt_aggagcaagcggagcagactgctgcacagcgact

-continued acatgaacatgacccccggaggcctggccccacccggaagcactaccag ccctacgccctcccagggatttcgccgcctaccggagcaaacggggca gaaagaaactcctgtatatattcaaacaaccatttatgagaccagtacaa actactcaagaggaagatggctgtagctgccgatttccagaagaagaaga aggaggatgtgaactgagagtgaagttcagcaggagcgcagacgcccccg cgtacaagcagggccagaaccagctctataacgagctcaatctaggacga agagaggagtacgatgtttttggacaagagacgtggccgggaccctgagat ggggggaaagccgagaaggaagaaccctcaggaaggcctgtacaatgaac tgcagaaagataagatggcggaggcctacagtgagattgggatgaaaggc gagcgccggaggggcaaggggcacgatggcctttaccagggtctcagtac agccaccaaggacacctacgacgcccttcacatgcaggccctgccccctc gc As described above, the CD25-CARs disclosed herein may be designed as a first generation, a second generation, a third generation, or a fourth or later next generation CAR (see Guedan et al. 2018; Smith et al. 2016). Further, the design of the non-specific CAR complex domains or regions described herein may be modified or optimized to incorporate different isoforms of the peptides described above or in accordance with guidance known in the art and/or as discussed in Guedan et al., which is incorporated herein in its entirety, as if fully set forth herein.

The CD25-CARs described herein may be expressed in a T cell or a population of T cells to generate CAR-T cells that can be administered to a patient suffering from a disease or condition associated with the expression of CD25. Expression of the CD25-CAR in a T cell or population of T cells is accomplished using any suitable expression system. In some embodiments, a CD25-CAR gene is cloned into a plasmid expression vector and transferred into a host T cell or population of T cells by electroporation.

In certain embodiments, the expression system is a retroviral packaging system. In such embodiments, an expression cassette that includes a CD25-CAR gene is cloned into a retroviral transfer plasmid vector and transferred into a packaging cell line (e.g., 293T cells, or a helper-free packaging cell line such as Phoenix) along with any other necessary plasm ids (e.g., envelope and/or packaging plasm ids) to allow the packaging cell line to produce retrovirus particles containing the desired CD25-CAR gene. Any suitable retroviral packaging system known in the art may be used in accordance with the embodiments described herein including, but not limited to, γ-retroviral packaging systems derived from a γ-retrovirus (e.g., MMLV (Moloney Murine Leukemia Virus), MSCV (Murine Stem Cell Virus), Murine Leukemia Virus (MLV)) or a lentiviral packaging system derived from a lentivirus (e.g., HIV). In certain aspects, the retroviral packaging system may be self-inactivating.

In certain embodiments, the expression cassette used to generate CAR-T cells as described above may include a nucleic acid sequence (i.e., CD25-CAR gene) that encodes any of the CD25-CARs described herein. In one embodiment, the expression cassette includes a CD25-CAR gene including SEQ ID NO:23. In another embodiment, the expression cassette includes a CD25-CAR gene that includes the nucleotide sequence below:

(SEQ ID NO: 24)
ctcgaggccaccatgtaccggatgcagctgctgagctgtatcgccctgtc tctggccctggtcacaaatagcgccctaccagcagcagcaccaagaaaa cacagctgcaactggaacacctcctgctggacctgcagatgatcctgaac ggcatcaacaactacaagaaccccaagctgacccggatgctgaccttcaa gttctacatgcccaagaaggccaccgagctgaagcacctccagtgcctgg aagaggaactgaagcccctggaagaagtgctgaatctggcccagagcaag aacttccacctgaggcctagggacctgatcagcaacatcaacgtgatcgt gctggaactgaaaggcagcgagacaaccttcatgtgcgagtacgccgacg agacagctaccatcgtggaatttctgaaccggtggatcaccttctgccag agcatcatcagcaccctgaccaccacgacgccagcgccgcgaccaccaac accggcgcccaccatcgcgtcgcagcccctgtccctgcgcccagaagcgt gccggccagcggcgggggcgcagtgcacacgaggggggctggacttcgcc tgtgatatctacatttgggcccctctggctggtacttgcggggtcctgct gctttcactcgtgatcactctttactgtaggagcaagcggagcagactgc tgcacagcgactacatgaacatgaccccccggaggcctggccccacccgg aagcactaccagccctacgccctcccagggatttcgccgcctaccggag caaacggggcagaaagaaactcctgtatatattcaaacaaccatttatga gaccagtacaaactactcaagaggaagatggctgtagctgccgatttcca gaagaagaagaaggaggatgtgaactgagagtgaagttcagcaggagcgc agacgcccccgcgtacaagcagggccagaaccagctctataacgagctca atctaggacgaagagaggagtacgatgtttttggacaagagacgtggccgg gaccctgagatggggggaaagccgagaaggaagaaccctcaggaaggcct gtacaatgaactgcagaaagataagatggcggaggcctacagtgagattg ggatgaaaggcgagcgccggaggggcaaggggcacgatggcctttaccag ggtctcagtacagccaccaaggacacctacgacgcccttcacatgcaggc cctgccccctcgctaa In some embodiments, the expression cassette may also include a promoter. Any suitable promoter may be used in the expression cassette including, but not limited to, human elongation factor 1α-subunit (EF1α), immediate-early cytomegalovirus (CMV), chicken β-actin (CBA) and its derivative CAG, the β glucuronidase (GUSB), or ubiquitin C (UBC). In one embodiment, the expression cassette is inserted cloned into a lentiviral transfer plasmid vector construct and includes an EF1α promoter and a CD25-CAR gene that includes the nucleotide sequence below (EF1α promoter=underlined):

(SEQ ID NO: 25)
gagtaattcatacaaaaggactcgcccctgccttggggaatcccagggac cgtcgttaaactcccactaacgtagaacccagagatcgctgcgttcccgc ccctcacccgcccgctctcgtcatcactgaggtggagaagagcatgcgt gaggctccggtgcccgtcagtgggcagagcgcacatcgcccacagtcccc gagaagttgggggagggggtcggcaattgaaccggtgcctagagaaggtg gcgcggggtaaactgggaaagtgatgtcgtgtactggctccgcctttttc -continued ccgagggtgggggagaaccgtatataagtgcagtagtcgccgtgaacgtt cttttcgcaacgggtttgccgccagaacacaggtaagtgccgtgtgtgg ttcccgcgggcctggcctctttacgggttatggcccttgcgtgccttgaa ttacttccacgcccctggctgcagtacgtgattcttgatcccgagcttcg ggttggaagtgggtgggagagttcgaggccttgcgcttaaggagccccctt cgcctcgtgcttgagttgaggcctggcttgggcgctggggccgccgcgtg cgaatctggtggcaccttcgcgcctgtctcgctgctttcgataagtctct agccatttaaaattttgatgacctgctgcgacgctttttttctggcaag atagtcttgtaaatgcgggccaagatctgcacactggtatttcggtttt ggggccgcgggcggcgacggggcccgtgcgtcccagcgcacatgttcggc gaggcggggcctgcgagcgcggccaccgagaatcggacgggggtagtctc aagctggccggcctgctctggtgcctggcctcgcgccgccgtgtatcgcc ccgccctgggcggcaaggctggcccggtcggcaccagttgcgtgagcgga aagatggccgcttcccggccctgctgcagggagctcaaaatggaggacgc ggcgctcgggagagcgggcgggtgagtcacccacacaaaggaaaagggcc tttccgtcctcagccgtcgcttcatgtgactccacggagtaccgggcgcc gtccaggcacctcgattagttctcgagcttttggagtacgtcgtctttag gttgggggggagggtttttatgcgatggagtttccccacactgagtgggtg gagactgaagttaggccagcttggcacttgatgtaattctccttggaatt tgccttttttgagtttggatcttggttcattctcaagcctcagacagtgg ttcaaagttttttttcttccatttcaggtgtcgtga ttcgaattcgccacc atgtaccggatgcagctgctgagctgtatcgccctgtctctggcctggt cacaaatagcgcccctaccagcagcagcaccaagaaaacacagctgcaac tggaacacctcctgctggacctgcagatgatcctgaacggcatcaacaac tacaagaaccccaagctgacccggatgctgacctcaagttctacatgcc caagaaggccaccgagctgaagcacctccagtgcctggaagaggaactga agcccctggaagaagtgctgaatctggcccagagcaagaacttccacctg aggcctagggacctgatcagcaacatcaacgtgatcgtgctggaactgaa aggcagcgagacaaccttcatgtgcgagtacgccgacgagacagctacca tcgtggaatttctgaaccggtggatcaccttctgccagagcatcatcagc accctgaccaccacgacgccagcgccgcgaccaccaacaccggcgcccac catcgcgtcgcagccctgtccctgcgcccagaagcgtgccggccagcgg cgggggggcgcagtgcacacgaggggggctggacttcgcctgtgatatctac atttgggcccctctggctggtacttgcggggtcctgctgctttcactcgt gatcactctttactgtaggagcaagcggagcagactgctgcacagcgact acatgaacatgacccccggaggcctggccccacccggaagcactaccag ccctacgcccctcccagggatttcgccgcctaccggagcaaacggggcag aaagaaactcctgtatatattcaaacaaccatttatgagaccagtacaaa ctactcaagaggaagatggctgtagctgccgatttccagaagaagaagaa ggaggatgtgaactgagagtgaagttcagcaggagcgcagacgcccccgc -continued
gtacaagcagggccagaaccagctctataacgagctcaatctaggacgaa gagaggagtacgatgttttggacaagagacgtggccgggaccctgagatg gggggaaagccgagaaggaagaaccctcaggaaggcctgtacaatgaact gcagaaagataagatggcggaggcctacagtgagattgggatgaaaggcg agcgccggaggggcaaggggcacgatggcctttaccagggtctcagtaca gccaccaaggacacctacgacgcccttcacatg caggccctgccccctcgctaa In certain embodiments, the expression cassette includes a pair of inverted terminal repeats (ITR) or long terminal repeats (LTR). In certain embodiments, the expression cassette also includes a polyadenylation signal (polyA).

A retroviral transfer plasmid vector construct that includes an expression cassette is provided in accordance with the embodiments described herein. In certain embodiments, the retroviral transfer plasmid vector construct includes an expression cassette that includes any CD25-CAR sequence in accordance with the embodiments described herein and in the examples below. The retroviral transfer plasmid vector construct, along with the rest of the retroviral expression system described above (if any) produce retroviral particles (e.g., γ-retrovirus particles or lentiviral particles) when introduced into the packaging cell line. The retroviral particles are then transfected into a host T cell or population of T cells, which results in expression of the CD25-CAR sequence in the host T cell or population of T cells.

In certain embodiments, a T cell or a population of T cells that express a CD25-CAR encoded by a CD25-CAR gene is provided in accordance with the embodiments described herein. In certain embodiments, the T cell or population of T cells express a CD25-CAR according to any embodiment described herein, which is encoded by a CD25-CAR gene in accordance with the embodiments described above. The T cell or population of T cells may be a primary T cell line or may be derived from any suitable commercially available T cell line. In one embodiment, the T cell or population of T cells is obtained from a human subject. In some embodiments, the T cell or population of T cells obtained from the subject are contacted with retroviral particles including a CD25-CAR gene that in turn cause the T cell or population of T cells to express a CD25-CAR encoded by the CD25-CAR gene. The CD25-CAR and corresponding CD25-CAR gene may be any such CD25-CAR or CD25-CAR gene in accordance with the embodiments described herein.

The T cell or population of T cells that express a CD25-CAR as described herein (also referred to herein is a CD25 CAR-T cell) may be used to treat a disease or condition that is associated with expression of CD25 or the IL-2 receptor. In certain embodiments, a method for treating the disease or condition includes a step of administering a population of T cells that express a CD25-CAR to a subject having the disease or condition. The population of T cells may be a population of T cells that expresses any CD25-CAR in accordance with the embodiments described herein.

In certain embodiments, the population of T cells administered to the subject are allogenic to the subject, i.e., the native T cells that are engineered to express the CD25-CAR are obtained from a donor subject that is different from the subject receiving the treatment. In other embodiments, the population of T cells administered to the subject are autologous to the subject, i.e., the native T cells that are engineered to express the CD25-CAR are obtained from the same subject that receives the treatment and subjected to an ex vivo procedure to engineer the CD25 CAR-T cells for use as a therapeutic. The population of native T cells may be obtained from the donor or subject receiving the treatment by blood draw, and the T cells are then separated from the other blood cells using any suitable procedure known in the art. The separated T cells are transfected with retroviral particles containing the CD25-CAR gene, thereby causing the T cell population to express the CD25-CAR gene by virtue of retroviral infection. The T-cells expressing the CD25-CAR are isolated, optionally expanded in vitro, and administered to the subject in accordance with the embodiments described herein.

Administration can be by any suitable method of delivering the T cell or population of T cells to an area where a target tissue or target cells express CD25 or IL-2 receptor. In certain embodiments, administration may be by infusion, and/or can be auricular, buccal, conjunctival, cutaneous, subcutaneous, endocervical, endosinusial, endotracheal, enteral, epidural, via hemodialysis, interstitial, intrabdominal, intraamniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronary, intradermal, intradiscal, intraductal, intraepidermal, intraesophagus, intragastric, intravaginal, intragingival, intraileal, intraluminal, intralesional, intralymphatic, intramedullary, intrameningeal, intramuscular, intraocular, intraovarian, intraepicardial, intraperitoneal, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intravenous, intraventricular, intravesical, intravitreal, laryngeal, nasal, nasogastric, ophthalmic, oral, oropharyngeal, parenteral, percutaneous, periarticular, peridural, rectal, inhalationally, retrobulbar, subarachnoid, subconjuctival, sublingual, submucosal, topical, transdermal, transmucosal, transplacental, transtracheal, ureteral, urethral, or vaginal. In certain embodiments the administration is by intravenous infusion into a blood vessel or injection into a target tissue or body cavity.

Diseases or conditions that may be treated in accordance with the embodiments described herein include, but are not limited to, a T cell malignancy or lymphoma, an autoimmune condition, or a transplant-associated condition associated with expression of CD25 or IL-2 receptors. In certain embodiments, the methods for treating the disease or condition may include a step of determining whether or confirming that the subject's cells express CD25. Lymphomas that may be treated in accordance with the embodiments described herein include, but are not limited to, Adult T-cell Leukemia Lymphoma, Peripheral T-cell Lymphoma, Cutaneous T-cell Lymphoma, Diffuse large B-cell Lymphoma, Follicular Lymphoma, Burkitt's Lymphoma, Anaplastic large cell Lymphoma, or Angioimmunoblastic T-cell Lymphoma. Autoimmune conditions, or transplant-associated conditions that may be treated in accordance with the embodiments described herein include, but are not limited to, graft-versus-host-disease, scleroderma, psoriasis, rheumatoid arthritis, or systemic lupus erythematosus.

"Treating" or "treatment" of a disease or condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression or remission of the condition, or some combination thereof. "Treating" a tumor also means that one or more hallmarks or markers of a tumor may be eliminated, reduced or prevented by the treatment.

In certain embodiments, the subject is preconditioned with one or more immunosuppressive chemotherapy drugs prior to CAR-T cell infusion. See, for example, U.S. Pat. No. 9,855,298, which is hereby incorporated by reference as if fully set forth herein.

From the foregoing, it will be appreciated that specific embodiments of the invention have been described herein for purposes of illustration, but that various modifications may be made without deviating from the scope of the invention. Accordingly, the invention is not limited except as by the appended claims. Additional background and embodiments related to the design, development, and use of the CD25-CARs the CD25-CAR genes, and the CD25 CAR-T cells described herein may be found in Guedan et al. 2018 and Smith et al. 2016, which are hereby incorporated by reference as if fully set forth herein.

EXAMPLES

The following examples are provided to better illustrate the claimed invention and are not to be interpreted as limiting the scope of the invention. To the extent that specific materials are mentioned, it is merely for purposes of illustration and is not intended to limit the invention.

Example 1: Generation of a γ-Retroviral Vector for Expressing a CD25-CAR (pMSGV-IL-2-ligand-h (28BBζ)-3rd-CAR)

An IL-2 ligand CAR-T (i.e., CD25-CAR T cell) may be constructed using an IL-2 ligand to engage the IL-2R (CD25) on malignant lymphomas that express the IL-2 receptor.

A CD25-CAR retroviral vector design using an MSGV retroviral vector plasmid was constructed comprising the following components: an MSGV retroviral backbone, an IL-2 ligand, the hinge and transmembrane regions of the CD8 molecule, the cytoplasmic portions of CD28 and 4-1BB, and the cytoplasmic component of the TCR molecule (pMSGV-IL-2-ligand-h(28BBζ)-3rd-CAR). An expression cassette including a nucleic acid sequence encoding IL-2 ligand, CD8, CD28, 4-1BB and TCR components was subcloned into an MSGV retroviral vector to produce the pMSGV-IL-2-ligand-h(28BBζ)-3rd-CAR retroviral vector (Creative Biolabs), the structure of which is shown in FIG. 1. The sequences of the components and expression cassette are shown below:

```
Amino Acid Sequence of IL-2-ligand
                              (SEQ ID NO: 21)
MYRMQLLSCIALSLALVTNSAPTSSSTKKTQLQLEHLLLDLQMILNGINN

YKNPKLTRMLTFKFYMPKKATELKHLQCLEEELKPLEEVLNLAQSKNFHL

RPRDLISNINVIVLELKGSETTFMCEYADETATIVEFLNRWITFCQSIIS

TLT

Nucleotide sequence of the CAR expression cassette
(IL-2-ligand-CD8 hinge and TM-CD28-4-1BB-CD3zeta)
                              (SEQ ID NO: 24)
ctcgaggccaccatgtaccggatgcagctgctgagctgtatcgccctgtc tctggccctggtcacaaatagcgcccctaccagcagcagcaccaagaaaa
```

-continued

```
cacagctgcaactggaacacctcctgctggacctgcagatgatcctgaac ggcatcaacaactacaagaaccccaagctgacccggatgctgaccttcaa gttctacatgcccaagaaggccaccgagctgaagcacctccagtgcctgg aagaggaactgaagcccctggaagaagtgctgaatctggcccagagcaag aacttccacctgaggcctagggacctgatcagcaacatcaacgtgatcgt gctggaactgaaaggcagcgagacaaccttcatgtgcgagtacgccgacg agacagctaccatcgtggaatttctgaaccggtggatcaccttctgccag agcatcatcagcaccctgaccaccacgacgccagcgccgcgaccaccaac accggcgcccaccatcgcgtcgcagccctgtccctgcgcccagaagcgt gccggccagcggcggggggcgcagtgcacacgaggggggctggacttcgcc tgtgatatctacatttgggcccctctggctggtacttgcggggtcctgct gctttcactcgtgatcactctttactgtaggagcaagcggagcagactgc tgcacagcgactacatgaacatgacccccccggaggcctggcccacccgg aagcactaccagccctacgcccctcccagggatttcgccgcctaccggag caaacgggggcagaaagaaactcctgtatatattcaaacaaccatttatga gaccagtacaaactactcaagaggaagatggctgtagctgccgatttcca gaagaagaagaaggaggatgtgaactgagagtgaagttcagcaggagcgc agacgcccccgcgtacaagcagggccagaaccagctctataacgagctca atctaggacgaagagaggagtacgatgtttttggcaagagacgtggccgg gaccctgagatggggggaaagccgagaaggaagaaccctcaggaaggcct gtacaatgaactgcagaaagataagatggcggaggcctacagtgagattg ggatgaaaggcgagcgccggaggggcaaggggcacgatggcctttaccag ggtctcagtacagccaccaaggacacctacgacgcccttcacatgcaggc cctgccccctcgctaa
```

```
Amino acid sequence of the CAR expression cassette
(IL-2-lidand-CD8 hinge and TM-CD28-4-1BB-CD3zeta
                                   (SEQ ID NO: 22)
MYRMQLLSCIALSLALVTNSAPTSSSTKKTQLQLEHLLLDLQMILNGINN

YKNPKLTRMLIFKFYMPKKATELKHLOCLEEELKPLEEVLNLAQSKNFHL

RPRDLISNINVIVLELKGSETTFMCEYADETATIVEFLNRWITFCQSIIS

TLTTTTPAPRPPTPAPTIASQPLSLRPEACRPAAGGAVHTRGLDFACDIY

IWAPLAGTCGVLLLSLVITLYCRSKRSRLLHSDYMNMTPRRPGPTRKHYQ

PYAPPRDFAAYRSKRGRKKLLYIFKQPFMRPVQTTQEEDGCSCRFPEEEE

GGCELRVKFSRSADAPAYKQGQNQLYNELNLGRREEYDVLDKRRGRDPEM

GGKPRRKNPQEGLYNELQKDKMAEAYSEIGMKGERRRGKGHDGLYQGLST

ATKDTYDALHMQALPPR
```

Figure 3:
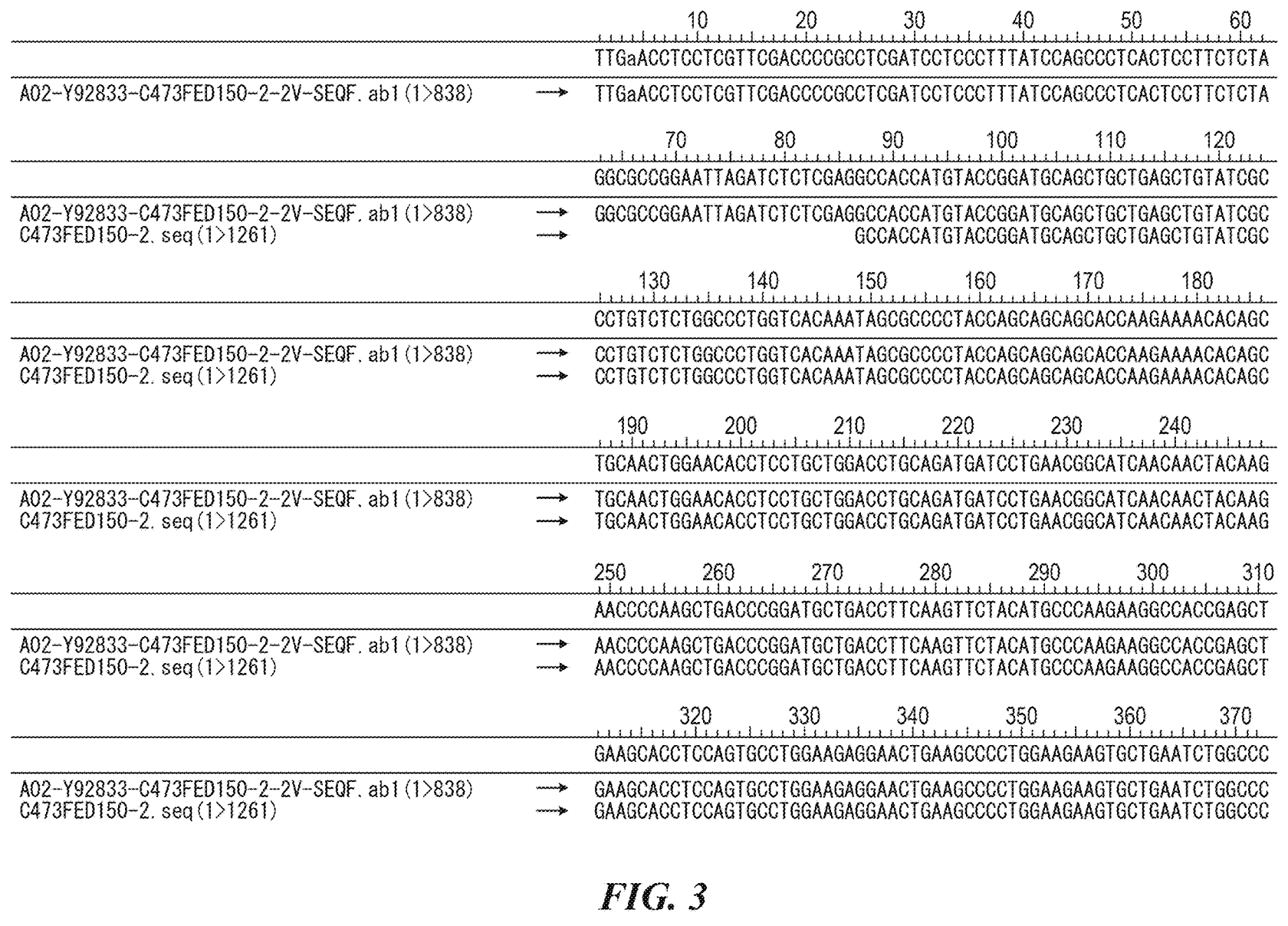

The insert encoding IL-2 ligand, CD8, CD28, 4-1BB and TCR components CAR expression was confirmed by Sanger sequencing (FIG. 3) and the expected fragment sizes for the construct were observed upon Restriction Digest (FIG. 2).

After packaging the pMSGV-IL-2-ligand-h(28BBζ)-3rd-CAR retroviral vector, the transduction efficiency was observed to be very low in HEK293 and primary T cells. Thus, development of the MSGV based retroviral vector above may be optimized or modified to improve transduction efficiency.

Example 2: Generation of a Lentiviral Vector for Expressing a CD25-CAR (pCDH-EF1a-IL-2-ligand-h(28BBζ)-3rd-CAR)

Figure 4:
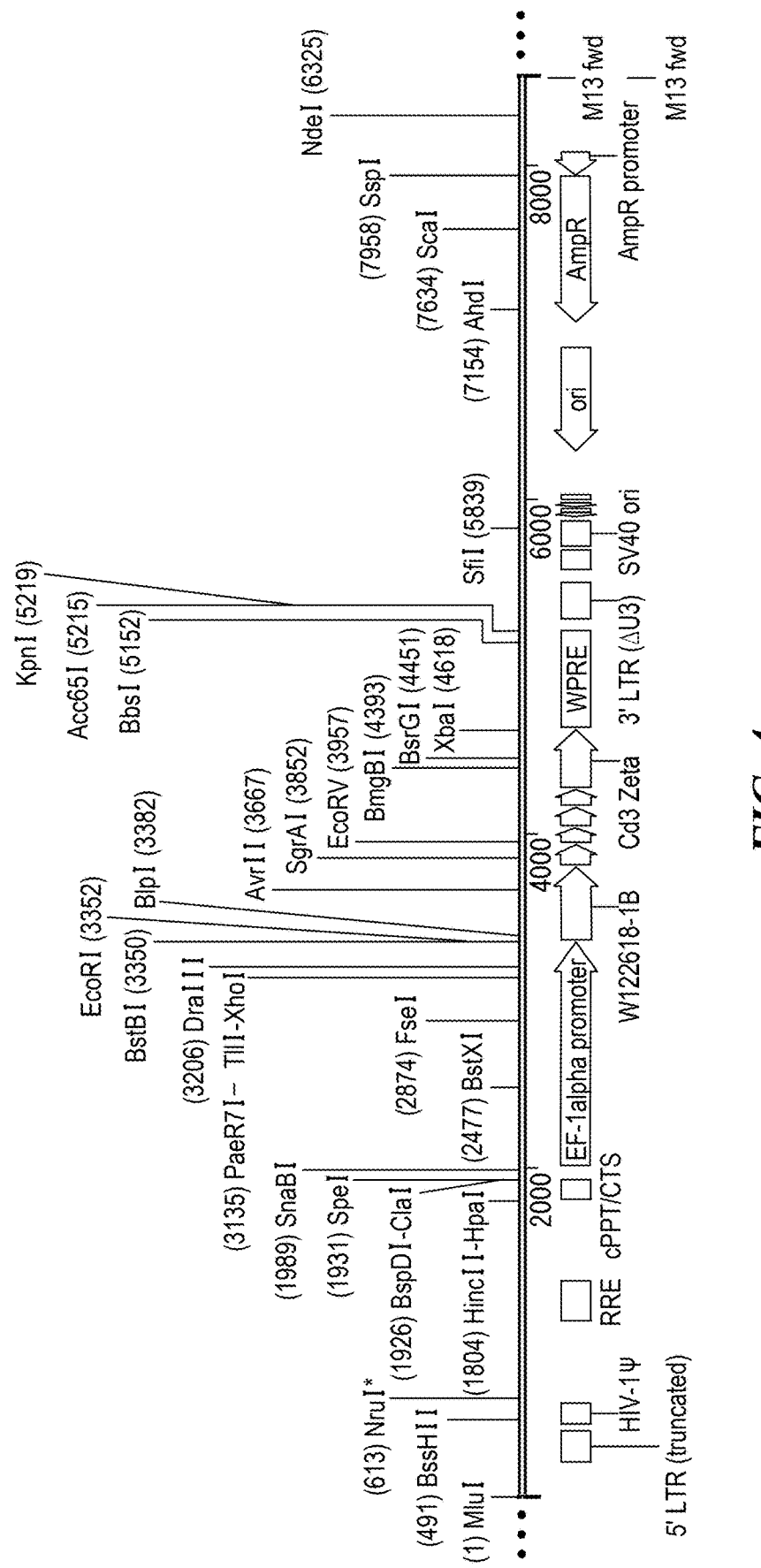
FIG. 4 is a schematic of the construction of lentiviral vector having a CD25-CAR gene insert (pCDH-EF1a-IL-2-ligand-h(28BBζ)-3rd-CAR).

Because of poor transduction efficiency, a lentiviral vector expressing the CD25-CAR was developed. The CD25-CAR lentiviral vector plasmid was constructed comprising the following components: an IL-2 ligand, the hinge and trans-membrane regions of the CD8 molecule, the cytoplasmic portions of CD28 and 4-1BB, and the cytoplasmic component of the TCR molecule (pMSGV-IL-2-ligand-h(28BBζ)-3rd-CAR). An expression cassette including an EF1a promoter and a nucleic acid sequence encoding IL-2 ligand, CD8, CD28, 4-1BB and TCR components was subcloned into a self-inactivating lentivirus vector to produce the pMSGV-IL-2-ligand-h(28BBζ)-3rd-CAR retroviral vector (Creative Biolabs), the structure of which is shown in FIG. 4. The sequences of the components and expression cassette are shown below:

```
Sequence of IL-2-ligand
                                   (SEQ ID NO: 21)
MYRMQLLSCIALSLALVTNSAPTSSSTKKTQLQLEHLLLDLQMILNGINN

YKNPKLTRMLIFKFYMPKKATELKHLOCLEEELKPLEEVLNLAQSKNFHL

RPRDLISNINVIVLELKGSETTFMCEYADETATIVEFLNRWITFCQSIIS

TLT
```

```
Nucleotide sequence of the CAR expression cassette
(EF1a-promoter-IL-2-ligand-CD8 hinge and
TM-CD28-4-1BB-CD3zeta)
                                   (SEQ ID NO: 25)
gagtaattcatacaaaaggactcgcccctgccttggggaatcccagggac cgtcgttaaactcccactaacgtagaacccagagatcgctgcgttcccgc cccctcacccgcccgctctcgtcatcactgaggtggagaagagcatgcgt gaggctccggtgcccgtcagtgggcagagcgcacatcgcccacagtcccc gagaagttggggggaggggtcggcaattgaaccggtgcctagagaaggtg gcgcggggtaaactgggaaagtgatgtcgtgtactggctccgccttttc ccgagggtggggagaaccgtatataagtgcagtagtcgccgtgaacgtt cttttcgcaacgggtttgccgccagaacacaggtaagtgccgtgtgtgg ttcccgcgggcctggcctctttacgggttatggcccttgcgtgccttgaa ttacttccacgcccctggctgcagtacgtgattcttgatcccgagcttcg ggttggaagtgggtgggagagttcgaggccttgcgcttaaggagcccctt cgcctcgtgcttgagttgaggcctggcttgggcgctggggccgccgcgtg cgaatctggtggcaccttcgcgcctgtctcgctgctttcgataagtctct agccatttaaaattttgatgacctgctgcgacgcttttttttctggcaag atagtcttgtaaatgcgggccaagatctgcacactggtatttcggttttt gggggccgcgggcggcgacggggcccgtgcgtcccagcgcacatgttcggc gaggcggggcctgcgagcgcggccaccgagaatcggacgggggtagtctc aagctggccggcctgctctggtgcctggcctcgcgccgccgtgtatcgcc ccgccctgggcggcaaggctggccggtcggcaccagttgcgtgagcgga aagatggccgcttcccggccctgctgcagggagctcaaaatggaggacgc ggcgctcgggagagcgggcgggtgagtcacccacacaaaggaaaagggcc
```

-continued

```
tttccgtcctcagccgtcgcttcatgtgactccacggagtaccgggcgcc gtccaggcacctcgattagttctcgagcttttggagtacgtcgtctttag gttggggggaggggttttatgcgatggagtttccccacactgagtgggtg gagactgaagttaggccagcttggcacttgatgtaattctccttggaatt tgcccttttgagtttggatcttggttcattctcaagcctcagacagtgg ttcaaagttttttcttccatttcaggtgtcgtgattcgaattcgccacc atgtaccggatgcagctgctgagctgtatcgccctgtctctggccctggt cacaaatagcgcccctaccagcagcagcaccaagaaaacacagctgcaac tggaacacctcctgctggacctgcagatgatcctgaacggcatcaacaac tacaagaaccccaagctgacccggatgctgaccttcaagttctacatgcc caagaaggccaccgagctgaagcacctccagtgcctggaagaggaactga agcccctggaagaagtgctgaatctggcccagagcaagaacttccacctg aggcctagggacctgatcagcaacatcaacgtgatcgtgctggaactgaa aggcagcgagacaaccttcatgtgcgagtacgccgacgagacagctacca tcgtggaatttctgaaccggtggatcaccttctgccagagcatcatcagc accctgaccaccacgacgccagcgccgcgaccaccaacaccggcgcccac catcgcgtcgcagccctgtccctgcgcccagaagcgtgccggccagcgg cgggggggcgcagtgcacacgagggggctggacttcgcctgtgatatctac atttgggcccctctggctggtacttgcggggtcctgctgctttcactcgt gatcactctttactgtaggagcaagcggagcagactgctgcacagcgact acatgaacatgaccccccggaggcctggccccacccggaagcactaccag ccctacgcccctcccagggatttcgccgcctaccggagcaaacggggcag aaagaaactcctgtatatattcaaacaaccatttatgagaccagtacaaa ctactcaagaggaagatggctgtagctgccgatttccagaagaagaagaa ggaggatgtgaactgagagtgaagttcagcaggagcgcagacgcccccgc gtacaagcagggccagaaccagctctataacgagctcaatctaggacgaa gagaggagtacgatgtgttttggacaagagacgtggccgggaccctgagatg gggggaaagccgagaaggaagaaccctcaggaaggcctgtacaatgaact gcagaaagataagatggcggaggcctacagtgagattgggatgaaaggcg agcgccggaggggcaagggggcacgatggcctttaccagggtctcagtaca gccaccaaggacacctacgacgcccttcacatgcaggccctgccccctcg ctaa
```

Amino acid sequence of the CAR expression cassette (IL-2-ligand-CD8 hinge and TM-CD28-4-1BB-CD3zeta)
(SEQ ID NO: 22)

```
MYRMQLLSCIALSLALVTNSAPTSSSTKKTQLQLEHLLLDLQMILNGINN

YKNPKLTRMLIFKFYMPKKATELKHLOCLEEELKPLEEVLNLAQSKNFHL

RPRDLISNINVIVLELKGSETTFMCEYADETATIVEFLNRWITFCQSIIS

TLTTTTPAPRPPTPAPTIASQPLSLRPEACRPAAGGAVHTRGLDFACDIY

IWAPLAGTCGVLLLSLVITLYCRSKRSRLLHSDYMNMTPRRPGPTRKHYQ

PYAPPRDFAAYRSKRGRKKLLYIFKQPFMRPVQTTQEEDGCSCRFPEEEE

GGCELRVKFSRSADAPAYKQGQNQLYNELNLGRREEYDVLDKRRGRDPEM
```

-continued

```
GGKPRRKNPQEGLYNELQKDKMAEAYSEIGMKGERRRGKGHDGLYQGLST

ATKDTYDALHMQALPPR
```

The insert encoding IL-2 ligand, CD8, CD28, 4-1BB and TCR components CAR expression was confirmed by Sanger sequencing (FIG. 6) and the expected fragment sizes of the construct were observed upon Restriction Digest (FIG. 5).

Lentivirus Packaging and Titering. The lentivirus was produced from the pCDH-EF1a-IL-2-ligand-h(28BBζ)-3rd-CAR vector transfected into 293T cells using the lentiviral packaging kit and transfection reagents from Creative Bio-labs following a polyethyleneimine (PEI) transfection protocol. The titer of the viral stock was then determined by Real-Time PCR. The cycle threshold (Ct) values are shown in Table 1 below:

TABLE 1

| Sample | Ct value | | | |
| --- | --- | --- | --- | --- |
| | WPRE | | ALB | |
| Lenti-CAR virus | 21.53 | 21.4 | 23.96 | 23.84 |

The number of lentiviral vector copies was measured by the standard curve created automatically by Roche 480 matched software (FIG. 7), and the lentiviral titer was calculated to be $1.62 \times 10^8$ TU/mL using the formula below:

$$\text{Lentivirus titer } (TU/\text{mL}) = \frac{(Copy_{WPRE} \div Copy_{ALB}) \times 2 \times Cell_{NO}}{Volume_{virus}}$$

Figure 9:
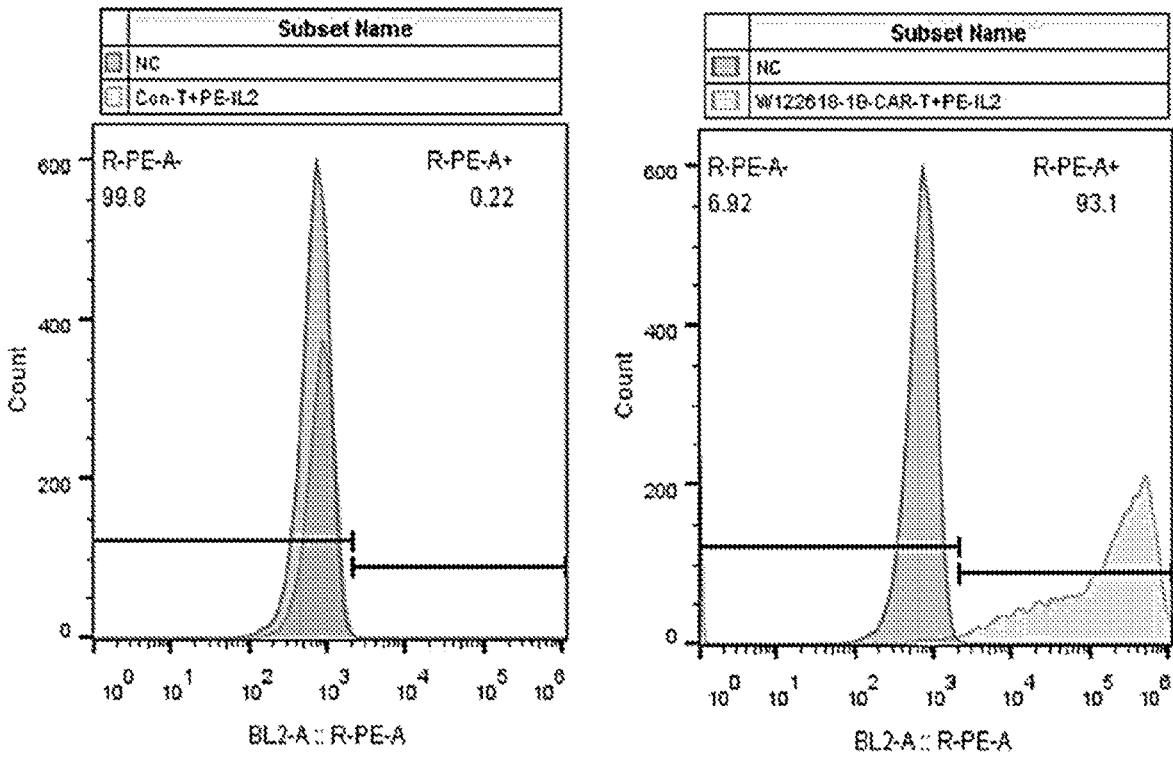
FIG. 9 shows pCDH-EF1a-IL-2-ligand-h(28BBζ)-3rd-CAR expression in primary T cells.

Cell Transfection. $2 \times 10^6$ Jurkat cells in logarithmic growth phase and $5 \times 10^5$ primary T cells isolated from PBMC were transfected with 100 μL or 50 μL concentrated lentivirus respectively. 6 μg/mL polybrene was added. Cells were cultured for another 48 h before FACS analysis by anti-IL-2 antibody. Transduction efficiency was very high. The positive rate of CAR expression in Jurkat cells was 86% (FIG. 8), and the positive rate of CAR expression in primary T cells was 93.1% (FIG. 9). Control group was cells without lentivirus transfection.

Example 3: Analysis of CAR-T Cells Expressing the pMSGV-IL-2-ligand-h(28BBζ)-3rd-CAR and Effects on Target CD25-Expressing Cells To analyze whether the CAR-T cells expressing the CD25-CAR activate target cells in vitro, two stable target cell lines were generated using Chinese hamster ovary (CHO) cells. Control target cells expressing a luciferase construct (CHO-S-Luciferase) and experimental target cells expressing a CD25 luciferase construct (CHO-CD25-Luciferase) were generated as follows.

Lentivirus Packaging. Fifteen cm culture dishes were prepared and inoculated with $5 \times 10^6$ CHO cells per culture dish in complete culture medium (high glucose DMEM, 10% FBS). Culture dishes were incubated at 37° C., 5% $CO_2$ in an incubator overnight.

The LVTransm transfection reagent and lentivirus packaging plasmids (Lenti-GOI, Lenti-packaging Mix) were defrosted at room temperature and thoroughly mixed by pipetting up and down. Next, 2 mL PBS was added into a well of a 6-well-plate followed by adding 10 μg Lenti-GOI and 30 μL Lenti-packaging Mix, respectively. Next, 50 μL LVTransm was added to the well and mixed well before incubation at room temperature for 10-15 min to form a complex.

The complex was added into a 15 cm culture dish dropwise and mixed well by waggling the dish back and forth. The culture dish was then incubated at 37° C., 5% $CO_2$ in an incubator for 6-8 hours. After 6-8 hours, the culture medium was refreshed. The culture dish was continuously cultured for 48 hours, the culture medium was harvested every 24 hours.

After 48 hours, the culture medium containing lentiviral particles was harvested and the supernatant was filtered using a 0.45 μm membrane. Next, the culture medium containing lentiviral particles was centrifuged at 50000×g for 2 hours at 4° C. After centrifugation, the supernatant was removed in a biocabinet, and 500 μL PBS buffer was added to resuspend the pellet. Following resuspension, the lentiviral particles were aliquoted and preserved at −80° C. The titer was detected using Quantitative PCR (Q-PCR).

Killing Curve. CHO cells were adjusted in logarithmic growth phase after cell recovery and seeded at a concentration of $5×10^4$ cells per well in a 24-well plate. The cells were Incubated overnight at 37° C. and 5% $CO_2$ in an incubator.

Following incubation, Puromycin was added to the culture medium at concentrations of 0.5 μg/mL, 1 μg/mL, 2 μg/mL, 4 μg/mL, 6 μg/mL, 8 μg/mL, and 10 μg/mL. Cells were observed daily for 3 days. The final Puromycin concentration used for stable cell line selection was 8 μg/mL, the concentration that was able to completely kill the cells after 3 days.

Stable Cell Line Selection. CHO cells were adjusted to a logarithmic growth phase after cell recovery and were seeded at a concentration of $5×10^6$ cells per well in a 6-well plate. The cells were then incubated at 37° C. and 5% $CO_2$ in an incubator overnight.

Lenti-Luciferase-EGFP-puro and CD25 lentiviruses were then added to the cells at a multiplicity of infection (MOI) of 2 for transfection. Cells were centrifuged at 800×g for 1 hour at 25° C. Following centrifugation, the cells were incubated for 24 hours at 37° C. and 5% $CO_2$ in an incubator.

After 24 hours, the medium was replaced with fresh medium and the cells were cultured for an additional 24 hours. Next, a puromycin medium was used to perform puromycin selection.

Figure 10:
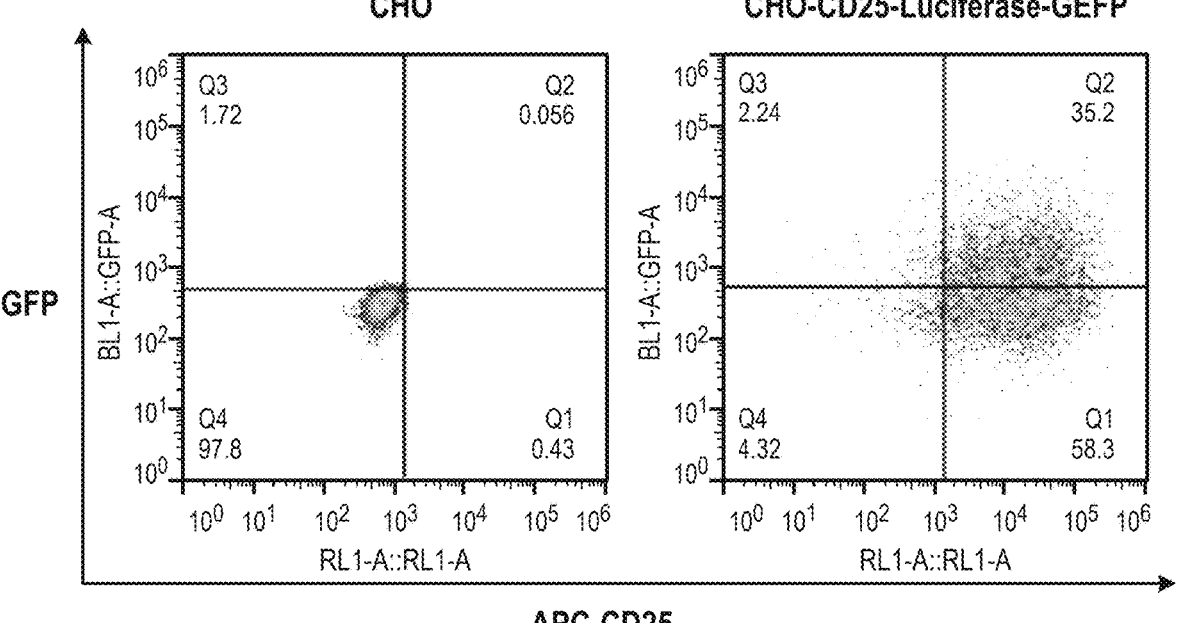
FIG. 10 shows two FACS plots showing expression of CD25 in control Chinese hamster ovary (CHO) cells (left) and CHO-CD25-Luciferase-EGFP target cells (right).

Cells were incubated in the puromycin medium for 5 days to killing untransfected cells via puromycin selection. Following purification, CD25 and luciferase expression were detected using FACS. An APC-anti CD25 antibody was incubated with CHO-CD25-Luciferase-EGFP target cells. FACS results showed that the positive rate of CD25 was 99% and the positive rate of GFP was 38% (FIG. 10). Double positive cells were 35% and could be used as target cells for co-culture experiments (FIG. 10).

Separation of T Cells from Peripheral Blood. Blood samples from healthy human donor peripheral blood were transferred into 15 mL sterile centrifuge tubes and centrifuged at 800×g for 20 minutes.

After centrifugation, the tubes were removed from the centrifuge gently without violent shaking or inverting the centrifuge tube. The pale-yellow serum in the upper layer was removed, and an equal volume of saline was added to the lower layer (the peripheral blood layer). The saline and peripheral blood layer were then gently mixed by inverting the centrifuge tube.

A lymphocyte separation solution was prepared and inverted upside down several times to mix well. Next, 5 mL of lymphocyte separation solution was added to a 15 mL centrifuge tube. The blood sample diluted in the second step was carefully pipetted along the tube wall to the upper layer of the lymphocyte separation reagent using a pipette to avoid mixing of the separation reagent and the blood sample. The tube was then centrifuged at 800×g for 20 minutes.

After centrifugation, the centrifuge tube was gently removed from the centrifuge. The white mononuclear cell layer in the middle of the tube was then drawn into a new sterile centrifuge tube an equal volume of saline was added to the tube, gently mixed, and centrifuged at 800×g for 5 minutes. After centrifugation, the supernatant was removed, and the PBMCs were washed once again. Cell density was adjusted to $5×10^7$ cells/mL, and the cells were transfer into a 2 mL cell cryotube.

Preparation of CAR-T Cells. First, Dynabeads were washed with PBS twice. The appropriate amount of Dynabeads were added to the PBMC, mixed gently, and incubated for 20 minutes at room temperature.

Next, a 2 mL cell cryotube was inserted into the magnetic pole and incubated for 1 minute at room temperature. Keeping the cryotube inserted in the hole of the magnetic pole, the tube was gently inverted to pour out the liquid in the tube.

The cell cryotube was removed from the magnetic pole, 3 mL of X-Vivo 15 medium (containing 200 IU/mL IL-2, 10 ng/mL IL7, 5 ng/mL IL-15) was added, and the cells and beads were resuspended with a pipette. Cell density was adjusted to 0.5-$1×10^6$ cells/mL.

Cells were incubated at 37° C. and 5% $CO_2$ in an incubator for 48 hours. Following incubation, cell density was adjusted to $1×10^6$ cells/mL. Cells were transfected using lentivirus expressing the pMSGV-IL-2-ligand-h(28BBζ)-3rd-CAR with MOI=20.

Polybrene was added to the prepared T cells in a final concentration of 6 μg/mL. Next, lentivirus was added to the prepared T cells and mixed thoroughly with a pipette, the culture vessel was sealed with a parafilm, and centrifuged at 800×g at room temperature for 1 hour.

After centrifugation, the culture was continued for 24 hours, and the medium was refreshed. After another 48 hours, the positive rate of CAR-T cells was detected by FACS.

For FACS analysis, primary T cells were transfected with lentivirus and CAR-T cells were collected as described. A PE-anti IL-2 antibody was incubated with the resultant cells. After incubation, a cytometer was used to detect the expression percentage of CAR-T cells. The control T cell (Con-T) group showed very low CAR-T at 0.87%, whereas the cells transfected with lentivirus expressing the pMSGV-IL-2-ligand-h(28BBζ)-3rd-CAR showed a very high percentage of CAR-T cells at 96.1% (FIG. 11). These results show that the prepared CAR-T cell surface can correctly express the constructed CAR and can be used for in vitro pharmacodynamic experiments.

Cytotoxicity of CAR-T Cells. First, target cells were adjusted into the logarithmic growth phase, and subcultured twice before performing the cytotoxicity experiment.

Target cells were resuspended in complete medium, and the cell density was adjusted to $2-5*10^5$ cells/mL. Using a new 96-well plate, the target cells were inoculated according to the amount of 100 μL/well. Unused wells around the 96-well plate were filled with 100 μL of sterile water per well to prevent evaporation of medium from the middle of the experimental wells. The well plates were placed in a 5% $CO_2$, 37° C. incubator and cultured overnight.

Following incubation, prepared CAR-T cells were collected by centrifugation and resuspend in 1640 medium with 10% FBS. The medium was removed from the 96-well plates, and the cells were gently washed once with sterile PBS. Then, the lysis experiment was carried out using 4 E/T ratios (1:1, 1:2.5, 1:5, and 1:10). The well plates were placed in a 5% $CO_2$, 37° C. incubator, and cultured for 24 hours. In the experiment, target cells were set as Maxi lysis and Mini lysis.

After the completion of the culture, the well plates were taken out from the incubator, and the ability of the recombinant CAR-T cells to lyse the target cells was examined by detecting the Luciferase activity (FIG. 12). The formula for calculating the percentage of target cell lysis is:

$$\text{Lysis} \% = \left(1 - \frac{RLU_{Sample}}{RLU_{Max}}\right) \times 100\%$$

Experimental groups cells expressing the CAR (W122618 CAR-T) showed a significant cytotoxic effect when co-cultured with target cells expressing CD25 (FIG. 12). There was no significant cytotoxic effect when control CHO cells were co-cultured with the experimental CAR-T (W122618 CAR-T) or control T (Con-T) cells.

Cytokine Detection. Target cells were adjusted into the logarithmic growth phase and subcultured twice before performing the experiment.

The target cells were resuspended in complete medium, and cell density was adjusted to 2-5*10^5 cells/mL. In a new 96-well plate, the target cells were inoculated with 100 μL/well. Unused wells around the 96-well plate were filled with 100 μL of sterile water per well to prevent evaporation of medium from the middle of the experimental wells. The well plates were placed in a 5% $CO_2$, 37° C. incubator and cultured overnight.

Prepared CAR-T cells were collected by centrifugation and resuspend in 1640 medium with 10% FBS. The medium was removed from the 96-well plates, and the cells were gently washed with sterile PBS once. Then, the cytokine secretion detection experiment was grouped into experimental and control groups as in the lysis test above. The well plates were placed in a 5% $CO_2$, 37° C. incubator, and cultured for 24 hours.

After the completion of the culture, the well plate was taken out of the incubator, centrifuged at 1200×g for 5 minutes at room temperature, and the supernatants were collected to detect the secretion of IL-2 and IFNγ by ELISA.

For the ELISA, A standard curve was generated measuring optical density (O.D.) compared to cytokine concentration (FIG. 13 upper). Cytokine levels were measured for IL-2 (FIG. 13, lower left) and IFNγ (FIG. 13, lower right) at a series of effector/target (E/T) ratios. These data showed that compared with the control group (Con-T cultured with target cells), all the experimental groups showed increased IL-2 and IFNγ when co-cultured with target cells (FIG. 13).

T Cell Proliferation. To quantify T cell proliferation, T cells were transfected with the control (Con-T) or the experimental (W122618-1B CAR-T) lentiviral vector. The first day after virus infection was recorded as day 1 (FIG. 14). CAR-T and control T cells were counted using tryptan blue staining, and the number of viable cells were counted. Cell proliferation was analyzed to day 8 (FIG. 14).

REFERENCES

The references, patents and published patent applications listed below, and all references cited in the specification above are hereby incorporated by reference in their entirety, as if fully set forth herein.

Dang et al. Phase II study of denileukin difitox for relapsed/refractory B-cell non-Hodgkin's lymphoma. J Clin Oncol 22(20):4095-4102 (2004).

Guedan et al. Engineering and Design of Chimeric Antigen Receptors. Mol Ther Methods Clin Dev 12:145-156 (2018).

Kochenderfer et al. Construction and preclinical evaluation of an anti-CD19 chimeric antigen receptor. J Immunother 32(7):689-702 (2009).

Matutes. Adult T-cell leukaemia/lymphoma. J Clin Pathol 60(12):1373-1377 (2007).

Smith et al. Chimeric antigen receptor (CAR) T cell therapy for malignant cancers: Summary and perspective. J Cell Immunother 2(2):59-68 (2016).

Williams et al. Structure/function analysis of interleukin-2-toxin(DAB486IL-2). Fragment B sequences required for the delivery of fragment A to the cytosol of target cells. J Biol Chem 265(20):11885-11889 (1990).

What is claimed is:

1. A chimeric antigen receptor (CAR) comprising:
a CD25 targeting component; and
a non-specific CAR complex comprising a hinge region, a transmembrane region, and an intracellular signaling domain,
wherein the CAR comprises an amino acid sequence of SEQ ID NO:22.

2. The CAR of claim 1, wherein the non-specific CAR complex further comprises one or more costimulatory domains.

3. The CAR of claim 1, wherein the CD25 targeting component is an IL-2 receptor ligand or a portion of at least 40 amino acids thereof.

4. The CAR of claim 3, wherein the IL-2 receptor ligand comprises human IL-2 (SEQ ID NO:21) or a portion of at least 40 amino acids thereof.

5. The CAR of claim 1, wherein the hinge region is an IgG based hinge region, or a CD8 hinge region, or a CD28 hinge region.

6. The CAR of claim 5, wherein
the IgG based hinge region comprises SEQ ID NO:1, SEQ ID NO:2, or SEQ ID NO:3, or a portion of at least 40 amino acids thereof;
the CD8 hinge region comprises SEQ ID NO:4, SEQ ID NO:5, or a portion of at least 40 amino acids thereof; or
the CD28 hinge region comprises SEQ ID NO:6 or a portion of at least 40 amino acids thereof.

7. The CAR of claim 1, wherein the transmembrane region is a CD3 transmembrane region, a CD28 transmembrane region, or a CD8 transmembrane region.

8. The CAR of claims 7, wherein
the CD3 transmembrane region comprises SEQ ID NO:7, SEQ ID NO:8, SEQ ID NO:9, or SEQ ID NO:10, or a portion of at least 40 amino acids thereof;
the CD28 transmembrane region comprises SEQ ID NO:11 or a portion of at least 40 amino acids thereof; or
the CD8 transmembrane region comprises SEQ ID NO:12, SEQ ID NO:13, or a portion of at least 40 amino acids thereof.

9. The CAR of claim 1, wherein intracellular signaling domain is a CD3-zeta (CD3ζ) intracellular signaling domain.

10. The CAR of claim 9, wherein the CD3ζ intracellular signaling domain comprises SEQ ID NO: 14 or a portion of at least 40 amino acids thereof.

11. The CAR of claim 2, wherein the one or more costimulatory domains is a CD28 costimulatory domain, an inducible costimulatory molecule (ICOS), a 4-1BB costimulatory domain, an OX40 costimulatory domain, or a CD27 stimulatory domain.

12. The CAR of claim 11, wherein
the CD28 costimulatory domain comprises SEQ ID NO:15 or a portion of at least 40 amino acids thereof;
the inducible costimulatory molecule (ICOS) comprises SEQ ID NO:16 or a portion of at least 40 amino acids thereof;
the 4-1BB costimulatory domain comprises SEQ ID NO:17 or a portion of at least 40 amino acids thereof;
the OX40 costimulatory domain comprises SEQ ID NO:18 or a portion of at least 40 amino acids thereof; or
the CD27 stimulatory domain comprises SEQ ID NO:19 or a portion of at least 40 amino acids thereof.

13. The CAR of claim 1, wherein the CAR is encoded by a nucleic acid sequence.

14. The CAR of claim 13, wherein the nucleotide sequence comprises SEQ ID NO:23.

15. The CAR of claim 13, wherein the nucleotide sequence is part of an expression cassette.

16. The CAR of claim 15, wherein the nucleotide sequence comprises SEQ ID NO:23, SEQ ID NO:24, or SEQ ID NO:25.

17. The CAR of claim 15, wherein the expression cassette is inserted in a γ-retroviral vector or a lentiviral vector.

18. A T cell or population of T cells that express the CAR of claim 1.

19. A method of treating a disease or condition comprising administering a population of T cells that express the CAR of claim 1 to a subject having the disease or condition.

* * * * *